(12) United States Patent
Van Meir et al.

(10) Patent No.: US 7,285,414 B2
(45) Date of Patent: Oct. 23, 2007

(54) VIRUSES TARGETED TO HYPOXIC CELLS AND TISSUES

(75) Inventors: Erwin G. Van Meir, Tucker, GA (US); Ainsley C. Nicholson, Lilburn, GA (US); Dawn E. Post, Duluth, GA (US)

(73) Assignee: Emory University, Atlanta, GA (US)

( * ) Notice: Subject to any disclaimer, the term of this patent is extended or adjusted under 35 U.S.C. 154(b) by 43 days.

(21) Appl. No.: 10/900,067

(22) Filed: Jul. 26, 2004

(65) Prior Publication Data
US 2005/0074430 A1    Apr. 7, 2005

Related U.S. Application Data

(63) Continuation-in-part of application No. 10/363,453, filed as application No. PCT/US01/30236 on Sep. 26, 2001, now abandoned.

(60) Provisional application No. 60/498,638, filed on Aug. 28, 2003, provisional application No. 60/235,283, filed on Sep. 26, 2000.

(51) Int. Cl.
| | |
|---|---|
| C12N 15/00 | (2006.01) |
| C12N 15/07 | (2006.01) |
| C12N 15/09 | (2006.01) |
| C12N 15/867 | (2006.01) |
| C12N 15/861 | (2006.01) |
| C12N 15/36 | (2006.01) |
| A61K 47/00 | (2006.01) |
| C12N 15/64 | (2006.01) |
| C12N 15/67 | (2006.01) |
| C12N 15/83 | (2006.01) |
| C12N 15/86 | (2006.01) |
| C12N 15/87 | (2006.01) |
| C12N 15/41 | (2006.01) |

(52) U.S. Cl. ............... 435/320.1; 435/91.4; 435/91.41; 435/91.42; 424/93.1

(58) Field of Classification Search ............. 435/320.1, 435/91.4, 91.41, 91.42; 424/93.1
See application file for complete search history.

(56) References Cited

U.S. PATENT DOCUMENTS 4,958,007 A    9/1990    Alroy et al.

(Continued)

FOREIGN PATENT DOCUMENTS

WO    WO95/24208 A1    9/1995

(Continued)

OTHER PUBLICATIONS

Ruan et al. (Neoplasm 1999, vol. 1, No. 5, pp. 431-437.*

(Continued)

*Primary Examiner*—Bruce R. Campell
*Assistant Examiner*—Bao Qun Li
(74) *Attorney, Agent, or Firm*—Greenlee, Winner, and Sullivan, P.C.

(57) ABSTRACT

The present invention relates to compositions comprising a novel recombinant virus which replicates selectively in cells or tissues that are hypoxic or have an activated HIF pathway. The novel compositions of the invention comprise a recombinant virus genetically engineered to have a hypoxia/HIF-responsive element, or a multiplicity of such elements, operably linked to a promoter which is in turn operably linked to a nucleic acid(s) encoding a peptide(s) which regulates or modulates replication of the virus and/or encode a therapeutic molecule. The invention also includes constructs useful for screening of agents which interact with proteins or genes in the hypoxia-inducible pathway or are jointly translated under hypoxia and animal models useful for monitoring a variety of hypoxic conditions in a non-invasive manner.

12 Claims, 21 Drawing Sheets

U.S. PATENT DOCUMENTS

| | | | |
|---|---|---|---|
| 5,382,427 | A | 1/1995 | Plunkett et al. |
| 5,401,490 | A | 3/1995 | Wiebe et al. |
| 5,482,923 | A | 1/1996 | Maione |
| 5,677,178 | A | 10/1997 | McCormick |
| 5,681,706 | A | 10/1997 | Anderson et al. |
| 5,728,379 | A | 3/1998 | Martuza et al. |
| 5,834,306 | A * | 11/1998 | Webster et al. .......... 435/320.1 |
| 5,840,686 | A | 11/1998 | Chader et al. |
| 5,843,404 | A | 12/1998 | Koch et al. |
| 5,846,528 | A | 12/1998 | Podsakoff et al. |
| 5,846,945 | A | 12/1998 | McCormick |
| 5,854,205 | A | 12/1998 | O'Reilly et al. |
| 5,858,351 | A | 1/1999 | Podsakoff et al. |
| 5,871,726 | A | 2/1999 | Henderson et al. |
| 5,882,914 | A | 3/1999 | Semenza |
| 5,942,434 | A | 8/1999 | Ratcliffe et al. |
| 5,952,226 | A | 9/1999 | Aebischer et al. |
| 5,977,058 | A | 11/1999 | Aggarwal et al. |
| 6,024,688 | A | 2/2000 | Folkman et al. |
| 6,046,031 | A | 4/2000 | Ni et al. |
| 6,080,578 | A | 6/2000 | Bischoff et al. |
| 6,124,131 | A | 9/2000 | Semenza |
| 6,130,071 | A | 10/2000 | Alitalo et al. |
| 6,174,861 | B1 | 1/2001 | O'Reilly et al. |
| 6,184,035 | B1 | 2/2001 | Csete et al. |
| 6,197,293 | B1 | 3/2001 | Henderson et al. |
| 6,211,163 | B1 | 4/2001 | Podsakoff et al. |
| 6,218,179 | B1 * | 4/2001 | Webster et al. .......... 435/320.1 |
| 6,222,018 | B1 | 4/2001 | Semenza |
| 6,288,024 | B1 | 9/2001 | Bouck et al. |
| 6,900,049 | B2 * | 5/2005 | Yu et al. .................. 435/320.1 |

FOREIGN PATENT DOCUMENTS

| | | | |
|---|---|---|---|
| WO | WO96/20276 | A1 * | 7/1996 |
| WO | WO98/05797 | | 2/1998 |
| WO | WO99/23216 | A2 | 5/1999 |
| WO | WO 00/15820 | | 3/2000 |

OTHER PUBLICATIONS

Minchenko A et al. Cell Mol Biol Res. 1994 vol. 40m, No. 1, pp. 35-39.*

Wei et al. J. Neuroviol. 1998, vol. 4, No. 2, pp. 237-241.*

Griga et al. Hepatogastroeenterology 2000, vol. 47, No. 36, pp. 1604-1607.*

Alemany, R. et al. (Jul. 2000) "Replicative Adenoviruses For Cancer Therapy;" *Nat. Biotech*. 18:723-727.

Bischoff, J.R. et al. (1996) "An Adenovirus Mutant That Replicates Selectively in p53-Deficient Human Tumor Cells;" *Science* 274:373-376.

Brown, J.M. et al. (1998) "The Unique Physiology of Solid Tumors: Opportunities (and Problems) for Cancer Therapy;" *Cancer Res*. 58:1408-1416.

Chapman, J.D. (1991) "Measurement of Tumor Hypoxia by Invasive and Non-Invasive Procedures: A Review of Recent Clinical Studies;" *Radiother. Oncol. Suppl*. 20:13-19.

Chapman, J.D. (1984) "The Detection and Measurement of Hypoxic Cells in Solid Tumors;" *Cancer* 54(11): 2441-2449.

Cuevas et al. (2003) "Specific Oncolytic Effect of a New Hypoxia-Inducible Factor-Dependent Replicative Adenovirus on von Hippel-Lindau-Defective Renal Cell Carcinomas," *Cancer Res*. 63:6877-6884.

De Fraipont, F. et al. (Sep. 2001) "Thrombospondins and Tumor Angiogenesis;" *TRENDS. Mol. Med*. 7(9): 401-407.

Goodrum. F.D. et al. (1998) "p53 Status Does Not Determine Outcome of E1B 55-Kilodalton Mutant Adenovirus Lytic Infection;" *J. Virol*. 72(12):9479-9490.

Grau, C. et al. (1988) "Effect of Cancer Chemotherapy on the Hypoxic Fraction of a Solid Tumor Measured Using a Local Tumor Control Assay;" *Radiother. Oncol*. 13:301-309.

Gray, L.H. et al. (1953) "The Concentration of Oxygen Dissolved in Tissues At The Time of Irradiation As A Factor In RadioTherapy;" *Br. J. Radiol*. 26(312): 638-648.

Hasegawa, T. et al. (1987) "Increase in Tumor $pO_2$ by Perfluorochemicals and Carbogen;" *Int. J. Radiat. Oncol. Biol. Phys*. 13:569-574.

He, T.C. et al. (1998) "A Simplified System for Generating Recombinant Adenoviruses;" *Proc. Natl. Acad. Sci*. 95:2509-2514.

Ido, A. et al. (Apr. 2001) "Gene Therapy Targeting for Hepatocellular Carinoma: Selective and Enhanced Suicide Gene Expression Regulated by a Hypoxia-Inducible Enhancer Linked to a Human. α.-Fetoprotein Promotor;" *Cancer Research* 61:3016-3021.

Jain, R. (1988) "Determinants of Tumor Blood Flow: A Review;" *Cancer Res*. 48:2641-2658.

Kaur et al. (2003) "Brain Angiogenesis Inhibitor 1 Is Differentially Expressed in Normal Brain and Glioblastoma Independently of p53 Expression," *Am. J. Pathol*. 162:19-27.

Kirn, D. (Dec. 2000) "Replication-Selective Oncolytic Adenoviruses: Virotherapy Aimed at Genetic Targets in Cancer;" *Oncogene* 19:6660-6669.

Markert, J.M. et al. (May 2000) "Conditionally Replicating Herpes Simplex Virus mutant, G207 for the Treatment of Malignant Glioma: Results of a Phase I Trial;" *Gene Ther*. 7:867-874.

O'Reilly, M.S. et al. (1994) "Angiostatin: A Circulating Endothelial Cell Inhibitor That Suppresses Angiogenesis and Tumor Growth;" *Cold Spring Harbor Symposia on Quantitative Biology* LIX:471-482.

Parker, J.N. et al. (Feb. 2000) "Engineered Herpes Simplex Virus Expressing IL-12 in the Treatment of Experimental Murine Brain Tumors;" *PNAS* 97:2208-2213.

DE Post and Van Meir (2001) "Generation of Bidirectional Hypoxia/HIF-Responsive Expression Vectors to Target Gene Expression to Hypoxic Cells," Gene *Therapy* 8:1801-1807.

Rodriguez, R. et al. (1997) "Prostate Attenuated Replication Competent Adenovirus (ARCA) CN706: A Selective Cytotoxic for Prostate-Specific Antigen-Positive Prostate Cancer Cells;" *Cancer Res*. 57:2559-2563.

Rothmann, T. et al. (1998) "Replication of ONYX-015, a Potential Anticancer Adenovirus, Is Independent of p53 Status in Tumor Cells;" *J. Virol*. 72(12):9470-9478.

Ruan, H. et al. (May-Jun. 2001) "A Hypoxia-Regulated Adeno-Associated Virus Vector for Cancer-Specific Gene Therapy;" *Neoplasia* 3(3):255-263.

Ruan, H. et al. "Use of Hypoxia-Related Gene Expression in Tumor-Specific Gene Therapy;" *Curr. Opin. Investig. Drugs* (Jun. 2001) 2(6):839-834.

Semenza et al. (1998) "From Molecular Biology to Cardiopulmonary Physiology," *Chest* 114:40S-45S.

Siemann, D.W. et al. (1988) "Characterization of Radiation Resistant Hypoxic Cell Subpopulations in KHT Sarcomas. (ii) Cell Sorting;" *Br. J. Cancer* 58:296-300.

Sinkovics, J. et al. (1993) "New Developments in the Virus Therapy of Cancer: A Historical Review;" *Intervirology* 36:193-214.

Song, C.W. et al. (1987) "Increase in $pO_2$ and Radiosensitivity of Tumors by Fluosol-DA (20%) and Carbogen;"*Cancer Res*. 47:442-446.

Teicher, B.A. et al. (1990) "Classification of Antineoplastic Treatments by Their Differential Toxicity Toward Putative Oxygenated and Hypoxic Tumor Subpopulations *in Vivo* in the FSaIIC Murine Fibrosarcoma;"*Cancer Res*. 50:3339-3344.

Vaupel, P. et al. (1987) "Blood Flow, Oxygen Consumption, and Tissue Oxygenation of Human Breast Cancer Xenografts in Nude Rats;"*Cancer Res*. 47:3496-3503.

Vaupel, P. et al. (1981) "Heterogeneous Oxygen Partial Pressure and pH Distribution in C3H Mouse Mammary Adenocarcinoma;" *Cancer Res*. 41:2008-2013.

Yang D.J. et al. (1995) "Development of F-18-Labeled Fluoroerythronitroimidazole as a PET Agent for Imaging Tumor Hypoxia;" *Radiology* 194(3):795-800.

Baron, U. et al. (1995) "Co-regulation of two gene activities by tetracycline via a bidirectional promoter"; *Nucleic Acids Res*. 23(17):3605-3606.

Dachs, G.U. et al. (1997) "Targeting gene expression to hypoxic tumor cells"; *Nature Medicine* 3(5):515-520.

Post, D.E. et al. (2003) "A novel hypoxia-inducible factor (HIF) activated oncolytic adenovirus for cancer therapy"; *Oncogene* 22:2065-2072.

Tanaka, T. et al. (1998) "Viral Vector-targeted Antiangiogenic Gene Therapy Utilizing an Angiostatin Complementary DNA"; *Cancer Research* 58(15):3362-3369.

Post and Van Meir (Oct. 2004) Brian Tumor Therapy Using Second Generation HYPR-Ads the Deliver Adjuvant Therapeutic Genes, Neuro-Oncology 6(4): 334 (Abstract ET-19, for Annual Meeting of the Society for Neuro-Oncology, Nov. 18-21, 2004).

Gullino, P.M. (1975) IN Vivo Utilization of Oxygen and Glucose by Neoplastic Tissue, Adv. Exp. Med. Biol. 75:521-536.

Kirikoshi et al. (2001) Expression of WNT10A in Human Cancer, International Journal of Oncology 19:997-1001.

Rosen et al. (1980) Stimulation by $N^6$, $O^2$ -Dibutyrl Cyclic Adenosine 3'-5'- Monophosphate of Ectopic Production of the Free β Subunit of Chorionic Gonadotropin by a Human Brain Tumor Cell Line, Cancer Research 40:4325-4328.

Takahasi et al. (May 2000) Hypoxic Induction of Prolyl 4-Hydroxylase a(l) in Cultured Cells, Journal of Biological Chemistry 274:14139-14146.

Uchiyama et al. (Apr. 2000) Hypoxia Induced Transcription of the Plasminogen Activator Inhjbitor-1 Gene Through Genstein-Sensitive Thyrosine Pathways in Vascular Endothelial Cells, Arteriocler. Thromb. Vasc. Biol. 20:1155-1161.

Wilkins et al. (1993) Inhibition of Lethal Damage Recovery by Cisplatin in a Brain Tumor Cell Line, Anticancer Research 13:2137-2142.

Minchenko et al. (May 2000) Regulation of endothelin-1 Gene Expression in Human Microvascular Endothelial Cells by Hypoxia and Cobalt: Role of Hypoxia Responsive Element, Mol. Cell. Biochem. 208:53-62.

\* cited by examiner

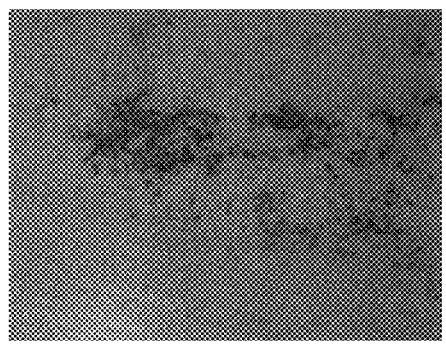 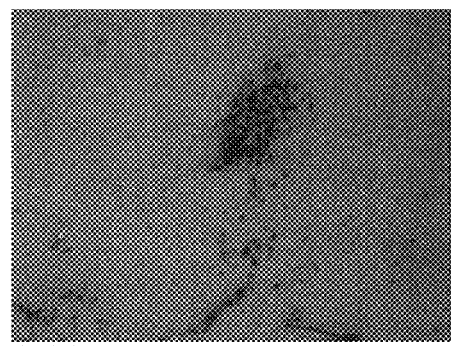
FIG. 12A  FIG. 12B

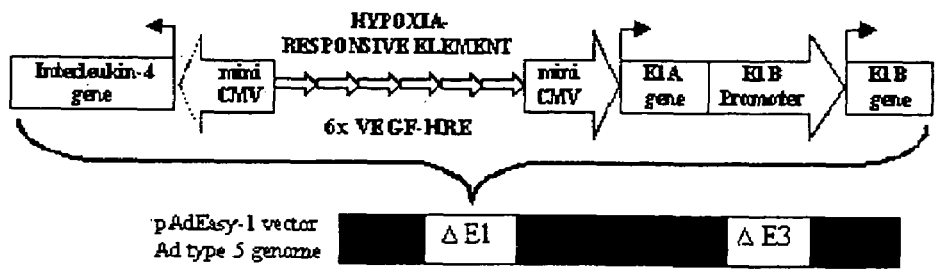
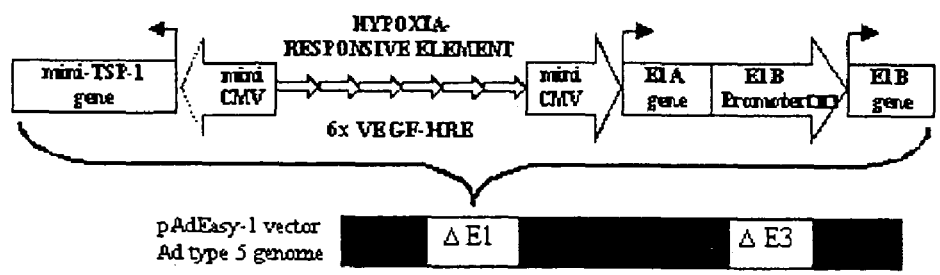
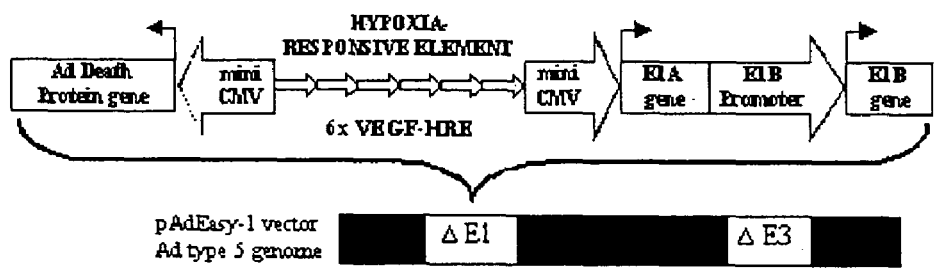
FIG. 13

US 7,285,414 B2

VIRUSES TARGETED TO HYPOXIC CELLS AND TISSUES

CROSS-REFERENCE TO RELATED APPLICATIONS

This application is a Continuation-in-part Application of U.S. application Ser. No. 10/363,453 filed Jul. 10, 2003, now abandoned and also claims benefit of U.S. Provisional Application No. 60/498,638 filed Aug. 28, 2003. U.S. application Ser. No. 10/363,453 is a National Stage Application of PCT International Application No. PCT/US01/30236, filed Sep. 26, 2001, which claims benefit of U.S. Provisional Application No. 60/235,283 filed Sep. 26, 2000, which is incorporated herein in its entirety to the extent not inconsistent herewith.

ACKNOWLEDGMENT OF GOVERNMENT FUNDING

This invention was made, at least in part, with funding from the National Institutes of Health under grant Nos. NS41403 and CA87830. Accordingly, the U.S. government may have certain rights in this invention.

FIELD OF THE INVENTION

This invention generally relates to novel recombinant viruses that selectively target cells in which the partial oxygen pressure is less than that normally found in that particular tissue type or which have an activated HIF (Hypoxia-Inducible Factor) pathway. The invention further relates to a virus that selectively replicates and is cytolytic in cells and tissues that are hypoxic or have an activated HIF pathway. Methods of treating cells or tissues that are hypoxic with the novel compositions of the invention are also provided. The invention further relates to screening assays for identifying compounds that modulate translation of a subset of mRNAs that are actively translated under hypoxia including the HIF mRNA, the hypoxia inducible factor pathway and animal models useful for non-invasive monitoring of cancer development, ischemia, efficacy of anti-cancer drugs, and any tissues or cells that are hypoxic.

BACKGROUND OF THE INVENTION

Cancer is one of the leading causes of death in industrialized countries. In the United States, cancer is the second leading cause of all deaths and accounts for hundreds of thousands of deaths each year. Cancer is a devastating disease on many levels. For example, gliomas are the main cause of death of patients with brain tumors. Patients with glioblastoma have a mean survival time of less than 12 months, and this prognosis has not changed much since 1959 (ten months) and 1932 (six to nine months) despite impressive developments in methods for treating cancer.

Cancer may be treated by a variety of methods including surgery, radiotherapy, chemotherapy, and immunotherapy. Although these methods of treatment have in general improved the survival rates of cancer victims, the fact remains that there is a clear need for improved therapeutic techniques for combating cancer.

A resurgent approach to treating cancer is referred to as virotherapy. Virotherapy first garnered the interest of scientists when it was discovered that tumors of some cancer patients regressed after they experienced viral infection or vaccination (see the reviews of Sinkovics, J., & Horvarth, J. [1993] Intervirology 36:193–214 and Alemany et al. [2000] Nat. Biotech. 18:723–727). Unfortunately, the initial promise of this approach was diminished when researchers discovered toxicity problems associated with virotherapy and furthermore the treatments had limited efficacy.

The advent of modern molecular biology has prompted scientists to reassess the feasibility of virotherapy. In particular, virus mediated gene therapy is now the central focus in the renewed interest in virotherapy. The molecular strategy underlying the design of virus mediated gene therapy systems is to deliver a gene which will inhibit tumor cell growth (e.g., controlling cell cycle or apoptosis), kill the cell (suicide gene), or induce an immune response (immunotherapy).

Two general approaches are available. One approach has centered on the use of replication-deficient viral vectors. The use of replication deficient vectors as virotherapeutic agents has encountered two major problems: (1) low in vivo transduction efficiency, resulting in poor gene delivery and (2) inability to specifically target tumor versus normal tissue.

Another approach to virotherapy involves the use of replication-competent viruses. The use of replication-competent viruses with a cytolytic cycle, has emerged as a viable strategy for directly killing tumor cells (oncolysis) as well as enhancing gene transfer and specifically targeting tumor cells. A variety of modified neuroattenuated herpes simplex viruses (HSVs) with deletions in the genes for neurovirulence ($y_1 34.5$) and ribonucleotide reductase ($U_L 39$), function as oncolytic agents for human tumor cells in vitro and in mouse models of human brain tumors in vivo. See, e.g., Parker et al. (2000) PNAS 97:2208–2213 and U.S. Pat. No. 5,728,379. In phase 1 clinical trials, twenty-one patients with malignant glioma have received intracranial injections of HSV G207 without any signs of encephalitis or CNS changes (Markert et al. [2000] Gene Ther. 10:867–874).

A different strategy makes use of an oncolytic, replication competent adenovirus (dl1520/ONYX-015) which has a deletion that leads to abrogated production of the 55 kDa E1B protein (Bischoff et al. [1996] Science 274:373–376; U.S. Pat. Nos. 6,080,578 and 5,677,178). Preliminary data suggested that the replication of this virus was restricted to tumor cells with a deficient p53 tumor suppressor gene. However, more recent findings have established that cells which are wild type for p53 gene status can also support replication of this virus (Rothmann et al. [1998] J. Virol. 72:9470–9478; Goodrun & Ornelles [1998] J. Virol. 72:9479–9490). This virus is currently being used in phase 1 clinical trials for ovarian cancer and gastrointestinal cancers that have metastasized to the liver, as well as in phase 2 and 3 clinical trials for recurrent and refractory head & neck cancer. Results so far have shown that injection of replication-competent adenovirus dl1520 is safe and well-tolerated by patients, whose complaints are mainly minor grade 1–2 flu-like symptoms (Kim [2000] Oncogene 19:6660–6669). The low toxicity of these two viral systems in humans suggests that replication-competent viruses are promising approaches for treating patients with tumors. More recently, the design of oncolytic viruses whose replication is restricted to a specific tumor type has been realized. An adenovirus (CN706) was created which showed a selective cytotoxicity for prostate-specific antigen (PSA) positive cancer cells in vitro and in murine prostate cancer models in vivo (Rodriguez et al. [1997] Cancer Res. 57:2559–2563; U.S. Pat. Nos. 5,871,726 and 6,197,293).

While such approaches utilizing replication-competent viruses are promising, they are limited in that: (1) multiple viruses would have to be created for different tumor types and possibly individual tumors due to the genetic heterogeneity of tumors, (2) they do not provide for the selective targeting of tumors derived from a broad range of tissues, and (3) they potentially require rigorous anti-viral treatments to eliminate virus after completion of therapy.

A multitude of U.S. patents have issued regarding hypoxia-inducible factor-1, virus mediated gene delivery, tissue specific constructs, and related topics.

Several patents to Semenza and Semenza et al. relate to hypoxia-inducible factor-1. U.S. Pat. No. 6,222,018 to Semenza discloses a substantially purified hypoxia-inducible factor (HIF-1) characterized as being capable of activating gene expression in genes that contain a HIF-1 binding site. U.S. Pat. No. 6,124,131 to Semenza discloses a substantially purified stable human hypoxia-inducible factor-1α as well as nucleotides encoding the same. U.S. Pat. No. 5,882,914 to Semenza discloses nucleic acids encoding hypoxia inducible factor-1 as well as purification and characterization of the expressed proteins.

The patents to Semenza and Semenza et al. refer to purified HIF-1, nucleic acids encoding HIF-1, antibodies that bind HIF-1, mutants of HIF-1, and method of using all of these biological molecules. The patents do not describe recombinant viruses that selectively replicate in and cytolyse hypoxic/HIF-active tissue and have the capability of delivering an anti-angiogenic factor or other proteins with anti-tumor activity. U.S. Pat. No. 6,218,179 to Webster et al. discloses tissue-specific hypoxia regulated constructs. Webster et al. describes a method for reducing ischemic injury to a cell exposed to hypoxic conditions. The constructs for reducing ischemic injury described in Webster et a comprise a chimeric gene containing a hypoxia responsive element, a therapeutic gene and a tissue-specific promoter. The therapeutic gene is selected so that its expression is effective in reducing ischemic injury to the cell. Examples of therapeutic genes are those for nitric oxide synthase, Bcl-2, superoxide dismutase and catalase. U.S. Pat. No. 5,834,306 to Webster et al. discloses a method and compositions comprising chimeric genes. The chimeric genes contain a tissue-specific promoter and a hypoxia responsive enhancer element, both of which are operably linked to a selected gene.

Recombinant adeno-associated virions and methods of using them are described in a series of patents to Podsakoff et al. U.S. Pat. No. 6,211,163 to Podsakoff et al. discloses methods for delivering DNA to the bloodstream using recombinant adeno-associated virus vectors. The invention is based on the discovery that recombinant adeno-associated virions are efficiently delivered to various muscle cell types and provide for the sustained production of therapeutic proteins. U.S. Pat. No. 5,858,351 to Podsakoff et al. discloses the use of adeno-associated virus virions for delivering DNA molecules to muscle cells and tissues. U.S. Pat. No. 5,846,528 to Podsakoff et al. discloses recombinant adeno-associated virus virions for delivering DNA molecules to muscle cells and tissues in the treatment of anemia. The Podsakoff et al. patents do not describe recombinant viruses which cytolyse hypoxic/HIF-active tissue and provide an anti-angiogenic factor or other proteins with anti-tumor activity.

U.S. patents related to the hypoxia-inducible factor-1 pathway describe a number of strategies. U.S. Pat. No. 6,184,035 to Csete et al. discloses methods for isolating, activating, and controlling differentiation from skeletal muscle stem or progenitor cells by using hypoxic conditions. The patent to Csete et al. relates to the discovery that adult skeletal muscle fibers cultured under hypoxic conditions give rise to greater numbers of progenitor cells as compared to muscle fibers grown under normal oxygen levels. U.S. Pat. No. 6,130,071 to Alitalo et al. discloses purified and isolated vascular endothelial growth factor-C cysteine deletion variants. U.S. Pat. No. 5,952,226 to Aebischer et al. discloses a device and method for delivery of EPO to a patient using an implanted device that continuously releases EPO. The invention described in the Aebischer et al. patent relates to providing EPO to a subject with cells engineered to express high levels of EPO under hypoxic conditions. U.S. Pat. No. 5,681,706 to Anderson et al. discloses genetic regulatory elements which effect anoxic induction of a DNA molecule in mammalian cells exposed to anoxia. U.S. Pat. No. 5,942,434 to Ratcliffe et al. discloses nucleic acid constructs comprising hypoxia response elements operably linked to a coding sequence such as genes for pro-drug activation systems or cytokines. As seen from these patents, the hypoxia-inducible pathway was harnessed for use in a specific context, recombinant viruses which selectively replicate in and cytolyse hypoxic tissue, or tissues with an activated HIF pathway, and further deliver adjuvant therapy, are not described in the prior art.

The following U.S. patents are expressly incorporated herein by reference to the extent that they are not inconsistent herewith: U.S. Pat. Nos. 6,222,018; 6,218,179; 6,211,163; 6,184,035; 6,130,071; 6,124,131; 5,952,226; 5,942,434; 5,882,914; 5,858,351; 5,846,528; 5,834,306, and 5,681,706.

Thus, there is a need for virotherapeutic systems which combine a therapeutic gene delivery approach and an oncolytic mechanism for the selective targeting of a wide variety of tumors.

A variety of particular problems were encountered during the discovery of this invention. Infection of cells by viruses is a complicated biochemical process. It was first necessary to show that tumor cells could be infected by a recombinant adenovirus under hypoxia. Next, hypoxia-induced expression of constructs in transfected tumor cell lines had to be demonstrated. The HIF-activated expression also had to have an appropriate $O_2$ concentration versus expression level profile. Hypoxia inducible constructs that bi-directionally express gene products had to be designed and tested for embodiments of the invention that involve delivery of adjuvant therapy. After these initial stages of designing and testing, recombinant viruses which contained the constructs were examined in transfected tumor cell lines for expression of E1A and E1B gene products. These expression studies demonstrated that hypoxia-dependent regulation seen in the transient reporter gene assay was maintained in the context of the viral genome. The next step in the invention involved demonstrating that the recombinant virus cytolyzed tumor cells in a hypoxia/HIF-active-dependent manner. Lastly, the inventors showed that the recombinant virus was delivered to brain tumors in a model system. Finally, these studies led to the recombinant virus of the invention.

SUMMARY OF THE INVENTION

The present invention provides compositions comprising a novel recombinant virus which replicates selectively in cells or tissues that are hypoxic or have an activated HIF pathway. The novel compositions of the invention comprise a recombinant virus genetically engineered to contain a hypoxia-responsive element, or a multiplicity of such elements, operably linked to a promoter which is in turn operably linked to a gene or genes which regulate or modulate replication of the virus or encode a therapeutic molecule or both. The recombinant virus can be either cytolytic or non-cytolytic. Also included in the invention are constructs useful for screening for agents which interact with proteins or genes in the hypoxia-inducible pathway.

A first embodiment of the invention relates to compositions comprising a recombinant cytolytic virus which replicates selectivity in hypoxic cells or tissues, or cells or tissues that have an activated HIF pathway. The novel compositions of this embodiment comprise a recombinant virus genetically engineered to contain a hypoxia-responsive element, or a multiplicity of such elements, operably linked to a promoter which is operably linked to a gene or genes which regulate or modulate replication of the virus, wherein the virus has a cytolytic cycle. The novel recombinant virus of this embodiment selectively replicates in and cytolyses hypoxic cells or tissues, or cells or tissues that have an activated HIF pathway. Examples of viruses that have cytolytic cycles include, but are not limited to, cytolytic adenoviruses, in particular adenovirus serotype 5; cytolytic picornaviruses, e.g., polioviruses; and cytolytic herpesviruses and herpes-like viruses, e.g., herpes simplex virus.

A second embodiment of the invention relates to compositions comprising a hypoxia/HIF-dependent replicative virus that delivers a gene or genes selectively to cells or tissues that are hypoxic or have an activated HIF pathway. Compositions comprising the recombinant virus of this embodiment are genetically engineered to have a hypoxia-responsive element, or a multiplicity of such elements, operably linked to a promoter which is operably linked to at least one gene which regulates or modulates replication of the virus and a gene to be expressed. The novel recombinant virus of this embodiment targets hypoxic tissues or cells, including tumors, where they selectively replicate and deliver a gene or genes. According to this embodiment, an additional gene(s) included in the novel recombinant virus of the invention provides anti-tumor activity or serves as a reporter gene or otherwise modulates hypoxic tissues or cells. Examples of preferred genes that may be delivered by the novel compositions of the invention include, but are not limited to, adenovirus death protein, interleukin-4 (IL-4), thrombospondin-1 (TSP-1), and angiostatin.

A third embodiment of the invention relates to compositions comprising an hypoxia/HIF-dependent replicative oncolytic virus that delivers a gene or genes to cells or tissues that are hypoxic or have an activated HIF pathway. Compositions comprising the recombinant cytolytic virus of this embodiment are genetically engineered to contain a hypoxia-responsive element, or a multiplicity of such elements, operably linked to a promoter which is operably linked to gene(s) which regulate or modulate replication of the virus, wherein the virus has a cytolytic cycle. The novel recombinant virus of this embodiment targets hypoxic tissues or cells, including tumors, where they selectively replicate, deliver a gene, and cause cytolysis. According to this embodiment, an additional gene(s) may be included in the novel recombinant cytolytic virus of this embodiment which provides anti-angiogenesis activity or serves as a reporter gene or otherwise modulates hypoxic tissues or cells. Examples of preferred genes that may be delivered by the compositions of the invention include, but are not limited to, adenovirus death protein, interleukin-4 (IL-4), thrombospondin-1 (TSP-1), and angiostatin.

A fourth embodiment of the invention relates to a method of treating a condition or disease that is characterized by hypoxia or an activated HIF pathway. A preferred aspect of this embodiment relates to a method of treating an individual with cancer, for example, by administration a recombinant replication-competent adenovirus that displays tumor cell specific lysis (oncolysis) and also delivers adjuvant therapy, in the form of an anti-angiogenic factor, to the tumor microenvironment. This is accomplished through the administration of a viral construct comprising a hypoxia/HIF-dependent replicative adenovirus (HYPR-Ad) that expresses an anti-angiogenic factor under hypoxic conditions. In this method, the novel compositions of the invention have a synergistic effect in destroying hypoxic tumor tissues due to the effect of viral cytolysis and expression of an anti-angiogenic factor. Another aspect of this embodiment of the invention relates to inducing activation of the hypoxia/HIF pathway in a tissue followed by treatment with the recombinant virus of the invention. For example, an undesired tissue, i.e., fat or scar, can be treated with an agent that specifically induces the HIF pathway in the tissue. After treatment with the agent, the undesired tissue is susceptible to destruction by the recombinant virus of the invention.

In a fifth embodiment, the invention relates to compositions and methods useful for identifying compounds which modulate the hypoxia and HIF pathways as well as the cell translation machinery under hypoxia. It is known that under hypoxia a CAP independent mRNA translation machinery operates so that there is preferential translation of certain mRNAs under hypoxia. Such mRNAs contain internal ribosomal entry sites (IRES) that permit translation even when CAP-dependent translation is blocked. The screening assay disclosed herein can identify inhibitors of this CAP-independent translation machinery. A stably or transiently transfected cell containing an expression vector comprising a hypoxia/HIF-inducible promoter operably linked to a reporter gene is contacted with a test compound and assayed for expression of the reporter gene. If the level of expression of the reporter gene is altered in the presence of the test compound compared to that in the absence of the compound (i.e., control), the compound is identified as a modulator of the hypoxia and HIF pathway, or the translation machinery operating under hypoxia. In a preferred embodiment, the HIF drug discovery assay is a high throughput assay suitable for large numbers of test compounds, i.e., by using libraries of compounds. Libraries of compounds are commercially available or may be synthesized using known procedures by a person of ordinary skill in the art. The drug discovery assays of the invention can also be used to test extracts of biological tissues, i.e., plant, fungal, bacterial, and animal.

In a sixth embodiment, the invention relates to drug discovery assays in vivo. An expression vector comprising a hypoxia- or HIF-inducible promoter operably linked to a reporter gene is used to generate a tumor containing the vector in vivo. The tumor containing the vector is then used to assess the efficacy of a chemical or biological agent that specifically targets hypoxic or HIF-active tissue for destruction or disrupts the hypoxic/HIF induction pathway in vivo.

Also provided are cell lines and animal models that are useful for non-invasive monitoring of cancer development, ischemia, the efficacy of anti-cancer drugs, and any tissues or cells that are hypoxic or have an activated HIF pathway. In these instances, an expression vector comprising a hypoxia- or HIF-inducible promoter operably linked to a reporter gene is used to generate a stable cell line or a transgenic animal containing the vector in vivo. Examples of reporter genes useful for this application include luciferase gene, $\beta$-galactosidase gene, or genes encoding fluorescent proteins (green fluorescent protein, red fluorescent protein etc.). Luminescence or fluorescence can be detected non-invasively by a CCD (charge-coupled device) camera system on a live anesthetized animal.

The invention also contemplates the use of genetic elements responsive to stimuli other than hypoxia such as light (UV light, visible light), radiation (x-ray), pH, sound (radiowaves), redox status, metabolic status, hormonal response, and telomere shortening.

BRIEF DESCRIPTION OF THE FIGURES

FIGS. 3A and 3C show ability of constructs to bi-directionally express luciferase in response to hypoxia; FIGS. 3B and 3D show ability of construct to bi-directionally express β-Gal in response to hypoxia. See example 6 for further description and experimental details.

FIG. 4A shows ability of constructs to bi-directionally express luciferase in response to variable oxygen partial pressures. FIG. 4B shows β-Gal bi-directional expression in response to variable oxygen partial pressures. See example 6 for further description and experimental details.

FIG. 5A shows cells exposed to normoxic conditions and FIG. 5B shows cells exposed to hypoxic conditions. See Example 7 for further description and experimental details.

In FIG. 8A, Uninf. is the uninfected cell line, dl309 is the cell line infected with adenovirus which is wild-type in the E1 region and has mutations in the E3 region, CMV-E1 is the construct containing the constitutively active CMV promoter/enhancer and the E1 gene. In FIG. 8B U refers to uninfected cells, H refers to hypoxic conditions, and N refers to normoxic conditions. See example 10 for further description and experimental details.

FIG. 9A is uninfected cells under hypoxia, FIG. 9B is Ad-CMV-E1 infected cells under normoxia conditions, FIG. 9C is HYPR-Ad#1 under normoxia conditions, and FIG. 9D is HYPR-Ad#1 under hypoxia. See example 11 for further description and experimental details.

FIG. 11A is a graph showing the mean tumor volume of glioma cells in immunocompromised mice treated with HYPR-Ad#1. FIG. 11B shows the size and weight of tumors with various treatments. The results shown suggest that HYPR-Ad#1 reduces tumor growth by specifically causing cytolysis of infected hypoxic tumor cells. See Example 15 for details.

FIGS. 12A and 12B show the results of the in vivo evaluation of compounds modulating expression of hypoxia-responsive genes. See Example 14 for further description and experimental details.

FIG. 13 shows schematic diagrams of HYPR-Ad vectors used to prepare the recombinant viruses to express mini-TSP-1, ADP, and IL-4 peptides. These vectors contain a bi-directional hypoxia/HIF responsive promoter such that a peptide of interest can be expressed under the CMV mini promoter as indicated on the left of the diagram. See Example 16 for further details.

DETAILED DESCRIPTION OF THE INVENTION

Figure 1:
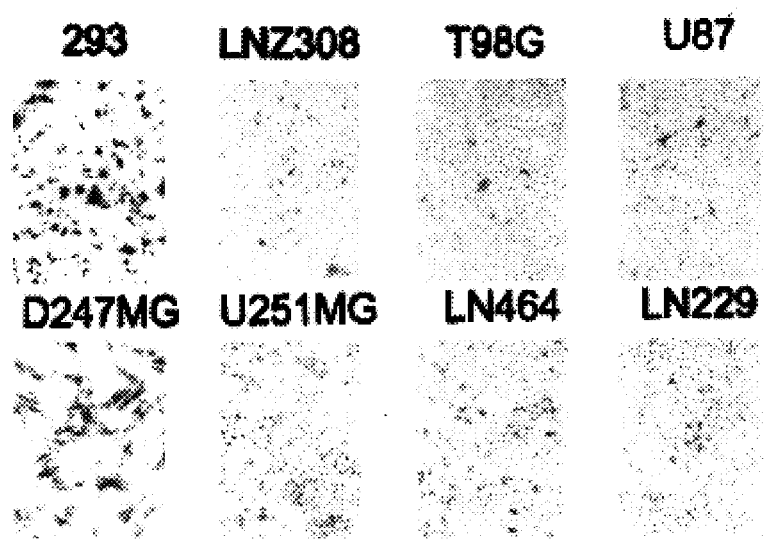
FIG. 1 shows the infection of tumor cells with recombinant adenovirus. The various cell lines indicated on the top of the panels were infected with recombinant adenovirus containing a LacZ reporter and stained for β-gal activity. See Example 1 for further description and experimental details.

The present invention was based on the discovery of the inventors that viruses genetically engineered to have a protein essential for viral replication under the control of a hypoxia and/or HIF responsive element/promoter construct selectively target and cytolyse hypoxic tissues or cells. The inventors further discovered that the novel recombinant viruses can be further engineered to selectively deliver a gene for diagnostic or therapeutic purposes to hypoxic/HIF-active tissues or cells.

The present invention provides compositions comprising recombinant viruses which replicate selectively in hypoxic/HIF-active cells. The novel compositions of the invention comprise recombinant viruses genetically engineered to have a hypoxia/HIF-responsive element operably linked to a promoter which is operably linked to a gene or genes which regulate or modulate replication of the virus and/or encode a therapeutic molecule. The compositions comprise recombinant viruses that may or may not have a cytolytic cycle. Viruses with a cytolytic cycle are preferred. The novel recombinant viruses of the invention selectively target any hypoxic tissues or cells that are hypoxic or in which the HIF pathway has been activated. Tumors that are hypoxic or contain a constitutively activated HIF pathway or have regions of hypoxia are preferred targets for the compositions of the invention.

A preferred embodiment of the invention relates to a recombinant replication-competent adenovirus that displays tumor cell specific lysis (oncolysis) and also delivers adjuvant therapy, with anti-tumor activity, to the tumor microenvironment. This is accomplished through the administration of a viral construct comprising a hypoxia/HIF-dependent replicative adenovirus (HYPR-Ad(s)) that expresses an anti-tumor factor under hypoxic/HIF-active conditions.

Another preferred embodiment of the invention relates to a method of treating a cancer patient with a tumor that is hypoxic, has an activated HIF pathway, or has regions of hypoxia/HIF activity by administering the composition of the invention. The method of the invention allows for the treatment of patients, including humans and animals, with a wide variety of tumors, so long as the tumors are hypoxic or have regions of hypoxia or have a constitutively activated HIF pathway. A specific method of this embodiment is directed to cancer patients that have tumors which were previously treated with chemo- or radiotherapeutic techniques and have become resistant to such treatments. Such chemo- and radiotherapeutic techniques are known to kill or destroy non-hypoxic tumor tissues, thereby allowing for survival of hypoxic tumor tissue. Thus the methods of the invention are suited for treating patients that have received previous or are currently receiving chemo- and radiotherapeutic treatments.

In general the terms and phrases used herein have their art-recognized meaning, which can be found by reference to standard texts, journal references and contexts known to those skilled in the art. The following definitions are provided to clarify their specific use in the context of the invention.

As used herein the term "normoxia" or "normoxic" refers to a normal level of oxygen or oxygen tension in a cell or tissues. The normoxic conditions employed in the experiments disclosed herein refer to the setting with the cell culture incubator at ambient partial pressure of about 20%.

As used herein the term "hypoxia" or "hypoxic" refers to a lower level of oxygen or oxygen tension in a cell or tissue compared to what is normally found. Cells or tissues are hypoxic when the $O_2$ concentration is lower than the normal level of oxygen in these particular cells or tissues.

As used herein the term "tumor hypoxia" or "hypoxic tumor cells" refers to a physiological difference in oxygen levels between normal and tumor tissue wherein the partial pressure of oxygen is reduced in the tumor tissue as compared to the normal tissue.

As used herein the term "cells or tissues with activated HIF" refers to cells or tissues in which the HIF transcription factor pathway is either constitutively active or in which it was activated by an exogenous stimulus or treatment. A number of agents are known to those of ordinary skill in the art to activate the HIF pathway and include, but are not limited to, iron chelators, cobalt, proteosome inhibitors, and geldanamycin.

As used herein the term "oncolytic" or "oncolysis" refers to the ability to lyse or destroy cancer or tumor cells.

As used herein the term "cytolytic" or "cytolysis" or "cytolyse" refers to the ability to lyse or destroy a cell or cells.

As used herein the term "anti-angiogenic" or "anti-angiogenesis" refers to the capability of inhibiting angiogenesis. Inhibitors of angiogenesis may be a gene or a protein which acts either directly or indirectly to modulate angiogenesis. Inhibitors of angiogenesis include, but are not limited to, angiostatin, anti-angiogenic peptides, anti-angiogenic antisense DNA, and other anti-angiogenic factors known to those skilled in the art.

As used herein the term "anti-tumor" or "anticancer" refers to the capability to destroy or reduce the size of a tumor or cancerous growth.

A nucleotide sequence is operably linked when it is placed into a functional relationship with another nucleotide sequence. For instance, a promoter is operably linked to a coding sequence if the promoter effects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous. The promoter is a DNA fragment which includes sequences sufficient to cause transcription of an associated (downstream) sequence.

The term "expression vector" as used herein is intended to indicate a DNA construct prepared for introduction into a prokaryotic or eukaryotic cell and typically comprises a replication system (i.e. vector) recognized by the host, including the intended DNA fragment encoding the desired polypeptide, and preferably also include transcription and translational initiation regulatory sequences operably linked to the polypeptide-encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1995) *Current Protocols in Molecular Biology*, Greene Publishing and Wiley Interscience, New York; and Metzger et al. (1988) *Nature,* 334: 31–36. Many useful vectors for expression in bacteria, yeast, fungal, mammalian, insect, plant or other cells are well known in the art and may be obtained from such vendors as Stratagene, New England Biolabs, Promega Biotech, and others. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, N.Y. (1983). Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

Drug Discovery Assays

In one embodiment, the invention relates to a method of identifying a compound which modulates the hypoxia-inducible pathway mediated induction of protein and/or gene expression. In this method, a cell line stably or transiently transfected with a vector comprising a hypoxia/HIF-inducible promoter operably linked to a reporter gene is used to detect compounds which modulate the expression of genes or any proteins modulated by hypoxia and/or HIF. In one aspect of this method, cell lines comprising a hypoxia/HIF-inducible promoter operably linked to a reporter gene can be used to detect compounds which inhibit expression of the reporter gene. It is preferred that expression of the reporter gene can be readily detected, e.g., by a simple calorimetric assay. Other genes which can be detected by other techniques such as enzymatic or fluorometric assays can be used as the reporter gene.

Compounds that test positive in the drug discovery assays of the invention are those that modulate the expression of the reporter gene. For example, cells are incubated with a test compound under specified conditions and compared to cells incubated under identical conditions except for the absence of that compound. A comparison between reporter gene expression with the test compound and reporter gene expression from the no-compound assay allows one to determine if the test compound is positive. Those test compounds which alter expression levels of the reporter gene compared to the no-compound (or other appropriate control) have tested "positive."

Materials that test positive in the drug discovery assays of the invention are useful for modulating the hypoxia/HIF pathway which is associated with a variety of clinical significant conditions, i.e., cancer, ischemia, and the like.

In certain aspects of this embodiment, the cells are lysed or further processed before it is contacted with the test compound. In any case, after the test compound is incubated for a selected period of time with the cell or portions thereof, the reaction mixture is assayed for level of reporter gene expression. In particularly useful aspects of this embodiment, the reporter gene expresses a protein that is readably detectable, e.g., an enzyme which catalyzes a reaction that is detected by a simple calorimetric assay or by other means such as monoclonal antibody detection. Examples of reporter genes useful in the invention include, but are not limited to, luciferase, β-galactosidase, alkaline phosphatase, green fluorescent protein, etc.

In a specific example, a vector comprising a hypoxia and/or HIF inducible promoter operably linked to a gene for alkaline phosphatase is stably or transiently transfected into a cell line. The cell lines comprising the vector are subjected to conditions which activate the hypoxia/HIF-inducible factor pathway and are contacted with a test compound. In general, when a test compound reduces or increases expression of alkaline phosphatase activity, it is identified as a hypoxia- and/or HIF-inducible pathway modulator. Test compounds which modulate expression of alkaline phosphatase activity have tested "positive" and are examined further.

The invention also relates to compositions comprising the compounds that test positive in the drug discovery assays of the invention.

Viruses

In general any virus may be used in the invention. Selection of the appropriate virus depends on a variety of factors such as the host to be treated. For example, treatment of a human requires a virus which can infect and replicate in *Homo sapiens*. Viruses that can be used to treat non-human subjects such as other mammals are also encompassed within the scope of the invention. Preferred viruses have a cytolytic cycle, i.e., the ability to lyse cells. Preferred cytolytic viruses are those of the adenovirus family. Examples of viruses from the adenovirus family include, but are not limited to, Adenovirus types 1–41, as described in the Catalogue of Animal Viruses & Antisera, Chlamydias & Rickettsias $6^{th}$ edition, 1990 from the American Type Culture Collection (ATCC). Other viruses suitable for use in the invention include, but are not limited to papillomaviruses, retroviruses, picornaviruses, e.g., polioviruses; herpesviruses and herpes-like viruses, e.g., herpes simplex virus; and others described in Catalogue of Animal Viruses & Antisera, Chlamydias & Rickettsias $6^{th}$ edition, 1990 from the American Type Culture Collection.

Recombinant Viruses

In general the recombinant viruses of the invention are genetically engineered to replicate selectively under hypoxic conditions. Recombinant viruses of the invention can be constructed by identifying genes that are responsive to oxygen partial pressures, i.e., genes that contain hypoxia responsive elements or hypoxia-inducible enhancer motifs (HRE). Using standard genetic engineering methods, any suitable promoter can be linked to HRE, which are then linked to a gene(s) in a particular virus that regulates or modulates virus replication. A variety of genes and/or their products are known to those skilled in the art that regulate or modulate viral replication. For example, the E1A gene product is known to encode an early viral protein essential for initiation of adenovirus replication. Thus this E1A gene of an adenovirus (or any structural or functional homolog) may be engineered to be put under the control of a hypoxia/HIF responsive element/promoter, thus creating an organism that selectively replicates under hypoxic/HIF-active conditions.

Gene Control Replication

Adenoviruses are DNA viruses that infect both dividing and quiescent cells. Re-entry of infected quiescent cells into the cell cycle is required for viral DNA replication and ultimately, viral progeny production. The expression of E1A gene products is essential for these viral functions and adenoviruses which lack the E1A gene region are replication-deficient. The adenoviral E1A gene is the first transcription unit to be expressed from a constitutively active promoter region. Products of the E1A gene exhibit a wide range of biological activities including the modulation of cellular and viral transcription (including the induction of E1B gene transcription) and the induction of DNA synthesis in quiescent cells. However, deregulation of cell growth control by E1A induces apoptosis through p53 dependent and independent mechanisms and ultimately interferes with viral progeny production. The prevention of apoptosis during wild type adenovirus infection is mediated by expression of the adenoviral E1B gene products. The E1B gene encodes two proteins, 21K and 55K, which function independently to inhibit E1A-induced apoptosis. The E1B 21K protein is homologous in sequence and function to the Bcl-2 family of apoptosis regulators and blocks E1A induced apoptosis as well as many other apoptotic stimuli. The infection of cells with adenoviruses lacking E1B 21K function leads to the appearance of extensive nuclear and viral DNA degradation (deg phenotype) and enhanced cytopathic effect (cyt phenotype). The E1B 55K, in conjunction with the adenoviral E4-orf6 gene product, has two functions during viral production: to directly interact with and inactivate p53, and later in viral production to facilitate the transport of viral late mRNA while inhibiting the transport of most cellular mRNA.

Recombinant viruses of the invention can be further engineered to contain a gene that allows for the termination of viral propagation with an exogenous agent, such as thymidine kinase, which would render them susceptible to ganciclovir. In addition, recombinant viruses can be further engineered so that the number of genes expressed is increased to four if internal ribosomal entry sites (IRES) are used to express two genes per transcription unit. According to this embodiment, a plurality of genes can be expressed in response to hypoxia or under conditions which activate the HIF-1 pathway.

Tumors and Hypoxia

Tumors, including, solid tumors are physiologically distinct from surrounding normal tissues and the tissues from which they are derived (Brown and Giaccia, 1998 Cancer Res. 58:1408–1426). An underlying difference in tissue vasculature between the normal tissue and the tumors is its unique physiological characteristics of poor oxygenation, or hypoxia. Tumor blood vessels are highly abnormal as a result of (1) the invading process of tumor cells on tissues containing normal vasculature and (2) the release of angiogenic factors by the tumors. Blood flow in solid tumors is often sluggish and leakier than that seen in normal tissues and is due to the abnormal nature of the tumor blood vessels. It is believed that these abnormal characteristics of tumor vascularization lead to the hypoxic physiological state of tumor tissues. A large body of evidence has suggested that hypoxic tumors are more resistant to radio- and chemotherapeutic treatments (See, e.g., Gray et al. 1953 Br. J. Radiol. 26:638–648; Teicher et al. 1990 Cancer Res. 50:3339–3344; Grau and Overgaard 1988 Radiother. Oncol. 13:301–309).

Regions of hypoxia in tumors have been shown to occur in many solid tumor model systems, see, e.g., Gullino, P. M., et al., Adv. Exp. Med. Biol. 75:521–536 (1975); Hasegawa, T., et al., Int. J. Radiat. Oncol. Biol. Phys. 13:569–574 (1987); Jain, R., et al., Cancer Res. 48:2641–2658 (1988); Siemann, D., et al., Br. J. Cancer 58:296–300 (1988); Song, C., et al., Cancer Res. 47:442–446 (1987); Vaupel, P., et al., Cancer Res. 47:3496–3503 (1987); Vaupel., P., et al., Cancer Res. 41:2008–2013 (1981). Tumors can also have an activated HIF pathway independent of hypoxia. Tumors associated with the Van Hippel Lindau syndrome comprising haemoglioblastoma, clear cell renal and carcinoma pancreatic and inner ear tumors are examples.

A variety of methods are available and known to one of skill in the art for detecting hypoxic tissues. See, for example, Chapman, J. D., Cancer, vol. 54, No. 11, pp. 2441–2449 (1984). Chapman, J. D., Radiother. Oncol., 20, pp. 13–19 (1991); Yang D J, et al., Radiology 194:795–800, 1995. U.S. Pat. Nos. 5,401,490 and 5,843,404 disclose methods of detecting hypoxia or hypoxic tissues and are hereby incorporated by reference. Any of these techniques or others known to those skilled in the art may be used to identify hypoxic tissues.

Angiogenesis

An essential component of tumor growth is angiogenesis, the establishment of new blood supply from preexisting vessels. Tumors disrupt physiological control over angiostasis to initiate neovascularization, a process triggered by the release of hypoxia-inducible angiogenic factors by tumors when they reach about 0.4 mm in diameter. Angiogenesis is a stepwise process during the malignant progression of astrocytoma and other cancers. In the development of gliomas, new blood vessels appear in low grade astrocytoma followed by an increase in density in anaplastic astrocytoma. During the transition from anaplastic astrocytoma to glioblastoma, extensive microvascular proliferation occurs, leading to abnormal vessels. Hypoxia is an integral component of astrocytoma progression and necrosis develops in its ultimate phase. Vascularity and microvascular cell proliferation are morphological features used to diagnose malignant astrocytomas from their less malignant counterparts and these features correlate with prognosis.

Targeting the vascular component of human tumors, including gliomas, provides a particularly effective cancer therapy because: i) it is estimated that about 100 tumor cells would be affected by the killing of each endothelial cell; ii) it is less likely that endothelial cells would become resistant to the treatment since they do not share the genetic instability of tumor cells; and, iii) strategies interfering with tumor vasculature have been used with success in animal models.

A variety of anti-angiogenesis agents can be used to enhance the effect of the recombinant virus of the invention. One of these inhibitors, angiostatin (see, e.g., U.S. Pat. No. 6,024,688, which is hereby incorporated by reference in its entirety, and O'Reilly et al., Cold Spring Harbor Symposia on Quantitative Biology, vol. LIX, pp. 471–482 (1994)), was used effectively against a variety of murine and human xenotransplanted tumors including gliomas, breast, prostate, and lung carcinomas. Moreover, angiostatin potentiates the anti-tumor effects of ionizing radiation by a combined cytotoxic effect on endothelial cells. The potent antitumor properties of angiostatin for use as a local adjuvant therapy can be delivered by the hypoxia-dependent oncolytic adenovirus of the invention.

Other angiogenesis inhibiting molecules include members of the thrombospondin (TSP) family of proteins. (See, e.g., de Fraipont et al., 2001, *Trends. Mol. Med.* 7(9):401–467.)

Several members of this family, TSP1 and TSP2, are known to have anti-angiogenesis activity. The anti-angiogenesis activity of the TSPs is localized to their procollagen and type 1 repeat (TSR) domains, a feature which other members of the family do not have. Thus, the recombinant virus of the invention can be engineered to have a TSP gene or a portion thereof (mini-TSP-1) under control of the hypoxia/HIF-responsive element. Since the anti-angiogenic activity is localized to a small portion of the protein, nucleic acids encoding the anti-angiogenic activity can be used in the invention.

Other angiogenesis inhibiting factors containing TSR domains that may be used in the invention are brain angiogenesis inhibitor 1 (BAI1), BAI2 and BAI3, (see Kaur et al. 2003 Am J Pathol. 162:19–27) and members of the ADAMTS family of proteins including, but not limited to, ADAMTS-1, 4, and 8 (see, e.g., U.S. Pat. No. 6,046,031). The number of anti-angiogenic genes is growing and any of these could be used in the invention.

Other genes which can be used in the invention include, but are not limited to, endostatin (see, e.g., U.S. Pat. Nos. 6,174,861 and 5,854,205), platelet factor-4 (PF4) (see, e.g., U.S. Pat. No. 5,482,923), interleukin-4 (IL4) (see, e.g., U.S. Pat. Nos. 5,382,427 and 4,958,007), and pigment epithelium-derived factor (PEDF) (see, e.g., U.S. Pat. Nos. 6,288,024 and 5,840,686). Genes encoding brain angiogenesis inhibitors (1,2,3), interleukin-12, tissue inhibitors of metalloproteinases, prolactin (10 kD fragment), bFGF soluble receptor, transforming growth factor beta, interferon alpha, placenta proliferin related protein, dominant negative fragments of vascular endothelial growth factor receptor or fragments thereof can also be used in the invention.

Antitumor Agents

A variety of genes which exhibit antitumor activity or enhance the antitumor activity of the virus or modulate an immune response against a tumor may be incorporated into the novel viral constructs of the invention. These antitumor agents operate by a variety of mechanism. For example, Bacillus thuringiensis subspecies thuringiensis has a protein named oncotoxin, which has antitumor activity (U.S. Pat. No. 5,977,058). The genes for proteins such as this may be genetically engineered into the novel recombinant viruses of the invention to enhance their antitumor activity. Other examples of antitumor agents include, but are not limited to, the various tumor suppressor genes that are know to those skilled in the art.

Other Agents

Other agents can be delivered by the recombinant virus of the invention for therapeutic purposes and include, but are not limited to, modulators of cell proliferation, cell cycle, cell growth, cell motility, apoptosis, immune response, metastasis, as are known to those of ordinary skill in the art.

Other Disorders

Hypoxic or HIF deregulation is associated with a number of mammalian diseases including, but not limited to arthritis, diabetic retinopathy, ischemic heart disease, stroke, tumors and pregnancy disorders (preclampsia and intrauterine growth retardation). The invention can be utilized to deliver a therapeutic gene(s) in such conditions. Moreover, it can be used to generate transgenic animals containing the reporter system for testing a variety of therapeutic agents to treat the aforementioned conditions.

Routes of Administration and Dosages

The novel compositions of the invention can be administered through a variety of routes including, but not limited to, subcutaneously, intraperitoneally, intravenously, ectopically, through aerosols, and intracerebrally. Routes of administration are known to those skilled in the art.

The novel recombinant viruses of the invention can be administered in a single dose or in multiple doses and more than one tumor in an individual needing treatment can be treated concurrently.

It should be understood that the detailed description and specific examples, while indicating preferred embodiments of the invention, are given by way of illustration only, since various changes and modifications within the spirit and scope of the invention will become apparent to those skilled in the art from the detailed description and specific examples.

EXAMPLES

Example 1

Infection of Tumor Cell Lines by Adenoviruses

This example shows brain tumor cell lines are efficiently infected by adenoviruses. The utilization of adenoviruses as gene therapy vectors for brain tumors is dependent upon viral entry. Infection of human cells with adenoviruses is a multistep process which involves specific interactions of at least two viral proteins and their respective cellular receptors. Brain tumors are histologically and genetically heterogeneous and, therefore, it is possible that only a small subset of these tumors can be infected by adenoviruses. To test this, the capacity of 8 human glioma cell lines (D247MG, U251MG, LN229, LN464, U87MG, LNZ308, T98G, U138MG) to be infected by adenovirus was examined using a replication-deficient adenovirus which contains a constitutively active exogenous LacZ reporter gene (AdLacZ, UNC-Virus Vector Core Facility, Chapel Hill, N.C.). Uninfected glioma cells and AdLacZ infected 293 human embryonic kidney cells were used as negative and positive controls, respectively.

Equal numbers of each cell line were seeded 24 h prior to infection. The cells were infected with AdLacZ at multiplicities of infection (MOI) ranging from 0.1–500 or were mock infected. 24 h post infection, cells were histochemically stained for β-galactosidase (β-gal) activity using the X-gal substrate and the number of infected (blue) cells at each MOI was visually quantified. The results are summarized in FIG. 1. Five of the eight cell lines achieved 75–100% infectivity at a MOI ranging from 100 to 500 while the remaining three cells lines (LNZ308, T98G, U138MG) infected less efficiently (<30%) even at an MOI of 500. The 293 cells infected at very high efficiency with the AdLacZ virus attaining 50% infection at a MOI of 1 and greater than 95% infection at a MOI of 5.

These results establish that a large subset (more than about 60%) of brain tumor cell lines can be infected by an adenovirus at high frequency. The differential susceptibility of human cancer cell lines to adenovirus infection is similar to that in other cell types, including human bladder and colon cancer cell lines.

Example 2

Effect of Hypoxia on Adenovirus Infection of Tumor Cell Lines

This example shows that adenovirus infection of brain tumor cell lines is not dramatically affected by hypoxia. The therapeutic efficacy of the HYPR adenovirus is dependent upon its ability to efficiently infect hypoxic tumor cells. The level of adenovirus infection under normoxic and hypoxic conditions in two genetically and biologically diverse glioma cell lines, D247MG and LN229, were compared. The cells were incubated for 72 h under normoxic (20.8% $O_2$) or hypoxic (1% $O_2$) conditions and then infected with a replication-deficient AdLacZ virus at several MOI's as described above. The cells were histochemically stained at 24 h post infection for β-gal activity and the percentage of infected (blue) cells was visually quantified (Table 1). It was found that the percentage of infected cells was slightly reduced under hypoxic conditions in D247MG (9% reduction) and LN229 (28% reduction) cells at sub-saturating MOI's. This was overcome by increasing the MOI to 250 for LN229, yielding 100% infected cells under normoxia and hypoxia. These experiments demonstrate that adenovirus infection under hypoxic conditions in cell culture occurs at levels similar to that under normoxic conditions. Thus, this efficiency permits virus multiplication and propagation since it is estimated that each infected cell will produce up to $10^3$–$10^4$ new viral particles.

TABLE 1

| | Percent blue cells/field | |
|---|---|---|
| | D247MG Cells | LN229 Cells |
| Normoxia | 35 (+/−6) | 78 (+/−6) |
| Hypoxia | 32 (+/−4) | 56 (+/−8) |

Example 3

Replication and Progeny Production of Adenovirus under Hypoxic Conditions

This example shows AdLacZ replication and progeny production are efficient under hypoxic conditions. The possibility that hypoxic cells will not allow high efficiency adenovirus replication and progeny production was tested in 293 cells using AdLacZ. The 293 cells are a human embryonic kidney cell line which complements, in trans, the viral functions missing in replication-deficient AdLacZ and allows viral production. Viruses were harvested from AdLacZ infected 293 cells grown under normoxic (20.8% $O_2$) and hypoxic (1% $O_2$) conditions and then used to infect D247MG and LN229 glioma cell lines under normoxia at several different MOI's. The cells were histochemically stained at 24 h post infection for β-gal activity and the percentage of infected (blue) cells was visually quantified and used as an estimate of viral titer. The results are summarized in Table 2. It was found that the percentage of infected (blue) cells was reduced by approximately 20% when the virus was produced in hypoxic 293 cells. These results suggest that viral production is only slightly reduced in hypoxic 293 cells.

TABLE 2

| | D247MG Cells | | LN229 Cells | |
|---|---|---|---|---|
| | % Blue cells/field | Inferred viral titer ($10^8$ pfu/ml) | % Blue cells/field | Inferred viral titer ($10^8$ pfu/ml) |
| Normoxia | 61 (+/−8) | 1.1 | 62 (+/−3) | 2.9 |
| Hypoxia | 49 (+/−5) | 0.9 | 56 (+/−8) | 2.6 |

In summary, the experiments described in Examples 1–3 demonstrate that a large subset of glioma cell lines can be infected with the recombinant adenovirus of the invention at high efficiency and that adenoviral infection, replication, and progeny production are not dramatically altered by hypoxic conditions.

Example 4

Construction of a Hypoxia/HIF-Responsive Promoter

This example describes the design and testing of a hypoxia/HIF-responsive promoter to be used for the generation of a hypoxia/HIF-dependent replicative adenovirus (HYPR-Ad's). The construction of the HYPR (hypoxia/HIF regulated) series of recombinant adenoviruses requires the hypoxia/HIF-dependent regulation of the adenoviral E1 gene region, which encodes proteins essential for efficient viral replication and progeny production. In addition, the generation of second generation HYPR-Ad's adenovirus requires the hypoxia/HIF-dependent regulation of a second gene (for example an anti-angiogenic gene) which confers adjuvant therapy. With these goals in mind, a bi-directional hypoxia/HIF-responsive promoter that co-regulates two gene activities (E1 and anti-tumor genes) were designed as shown below.

| ANTI-ANGIOGENIC GENE | MINIMAL PROMOTER | HYPOXIA-RESPONSE ELEMENTS | MINIMAL PROMOTER | E1 GENE |
|---|---|---|---|---|

Figure 2:
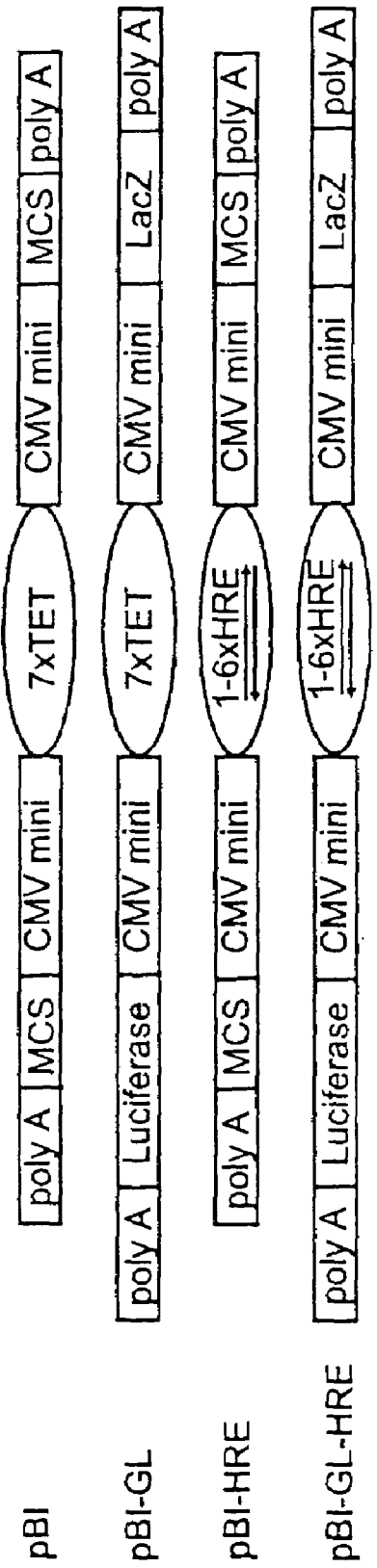
FIG. 2 shows schematic representations of plasmids used to construct the novel recombinant viruses of the invention. MCS refers to multiple cloning site; TET-tetracycline responsive elements; HRE-hypoxia and/or HIF responsive elements; 1–6 refers to the number of tandem copies of HRE. See examples 4 and 5 for further description and experimental details.
Figure 3A:
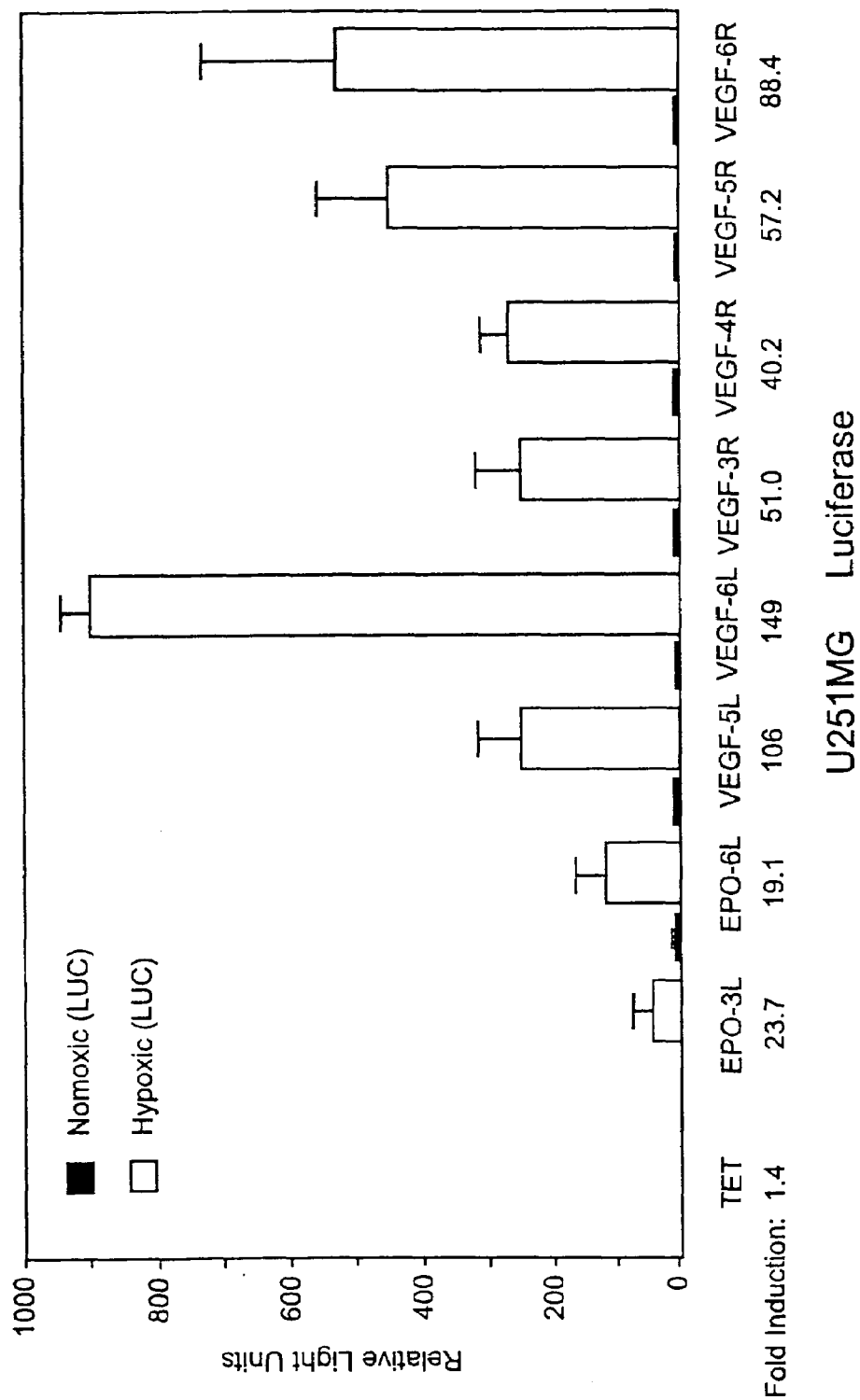
FIGS. 3A–D show the hypoxia induced expression of constructs in transfected tumor cell lines. VEGF or EPO-3,4,5,6 refers to the number of tandem repeats in the constructs, L for 5' orientation, and R for 3' orientation.
Figure 3B:
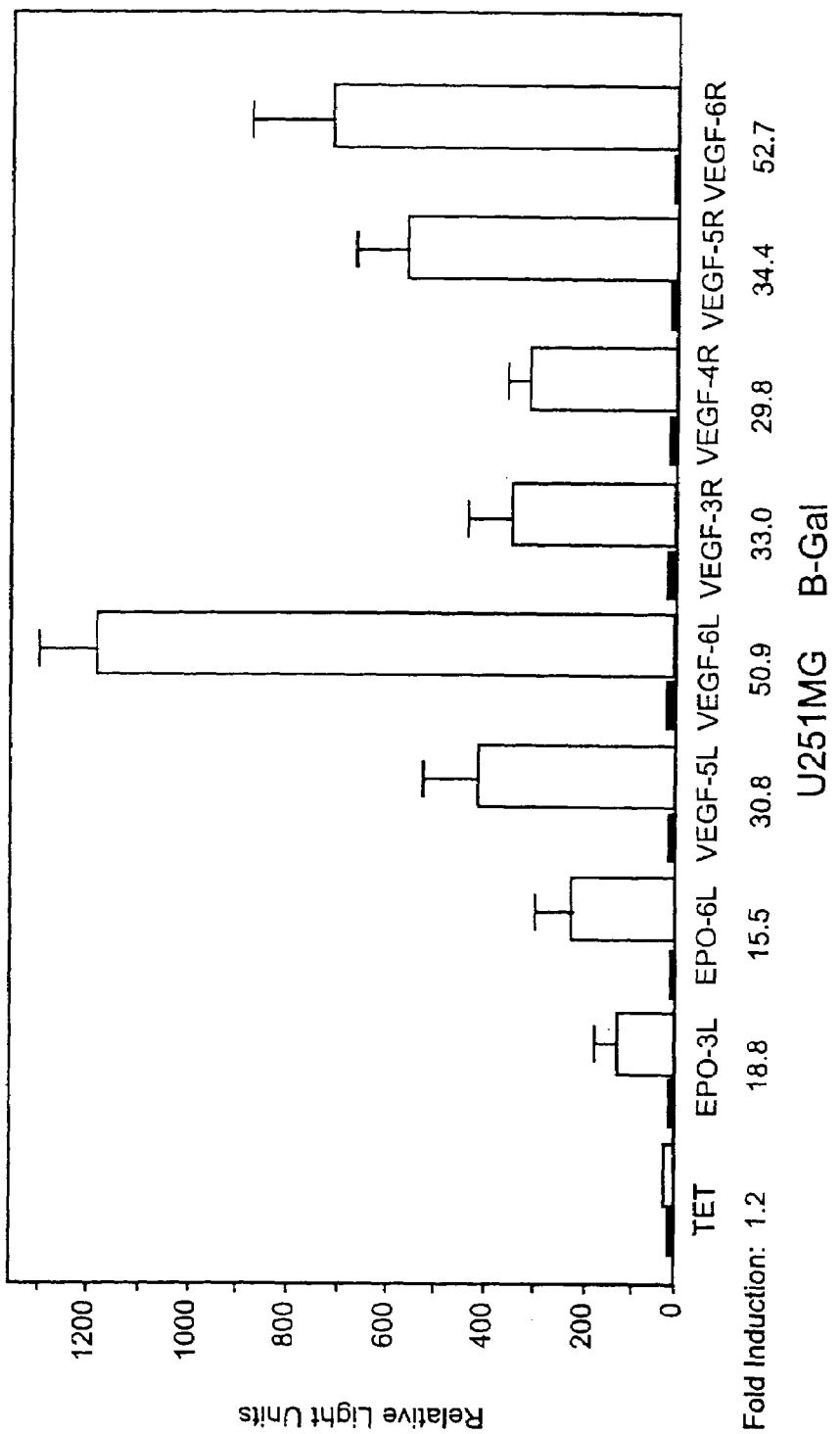
Figure 3C:
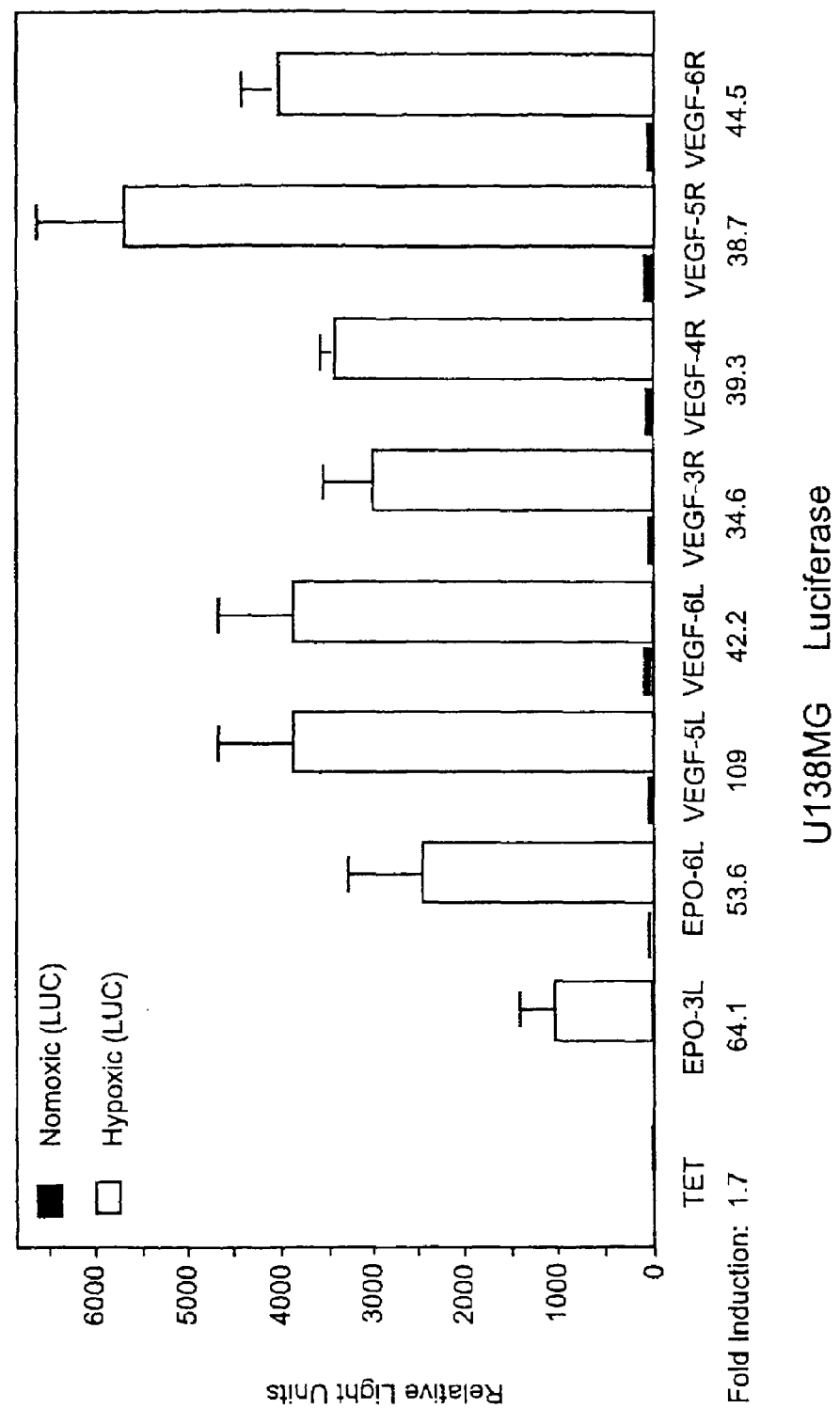
Figure 3D:
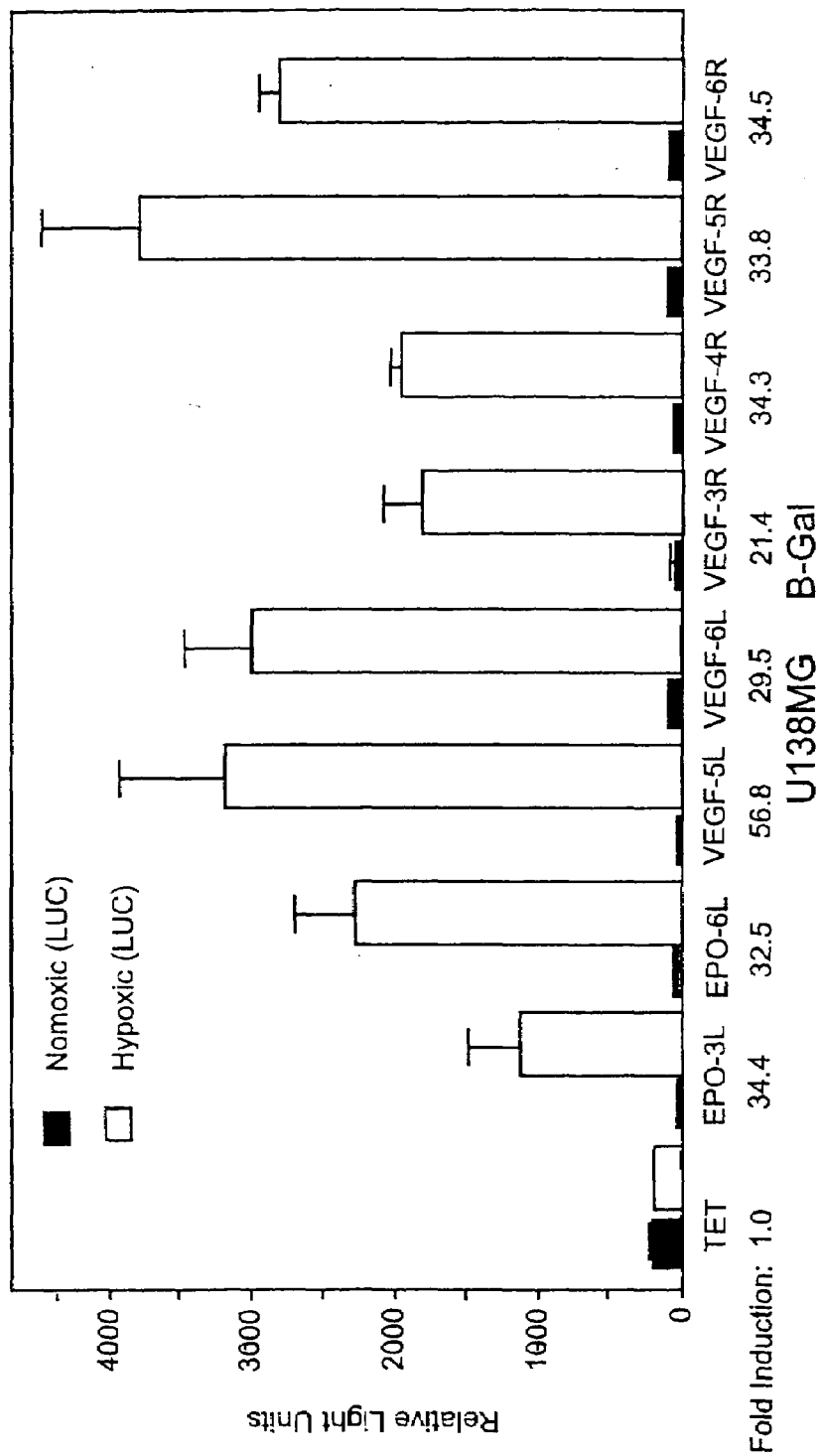

A commercially available mammalian expression vector (pBI, Clontech, Palo Alto, Calif., FIG. 2) was used as a starting material for the generation and testing of a bi-directional hypoxia/HIF-responsive promoter. The pBI plasmid contains a tetracycline-responsive element which allows conditional bidirectional expression of two heterologous genes. Hypoxia/HIF-responsive elements were identified in several genes (e.g. VEGF) and appeared to function as classical enhancer elements. Therefore, these elements were selected for these constructs to function bidirectionally to co-regulate the expression of two genes.

The first step in the construction of the HYPR virus was the selection of the hypoxia/HIF-responsive promoter. Hypoxic conditions are known to initiate a cascade of physiological responses and lead to the induction of genes involved in glycolysis, erythropoiesis, and angiogenesis. The HIF-1 protein complex, which is a heterodimer composed of the two basic helix-loop-helix proteins HIF-1α and HIF-1β, mediates transcriptional responses to hypoxia by binding to cis-acting hypoxia/HIF-inducible enhancer motifs (HRE) present within target genes. As part of the family of hypoxia-activated transcription factors, HIF2 and HIF3 have also been identified and found to be functionally similar to HIF1α. The HRE present within the 3'-flanking region of the erythropoietin (EPO) gene and 5'-flanking region of the VEGF gene are less than 50 bp in length. These HRE's contain highly conserved HIF-1 binding sites and other gene-unique cis-acting sequences that are functionally essential for hypoxic/HIF induction. EPO is a glycoprotein hormone produced in the kidney and liver in response to hypoxia and stimulates erythropoiesis by binding to its receptor expressed on erythroid progenitor and precursor cells. EPO and its receptor are also expressed in the central nervous system by astrocytes and neurons, respectively, where it is currently believed that they act in a paracrine fashion and function to protect neurons against hypoxia-induced damage. VEGF is induced by hypoxia in a variety of cell types and is also expressed by a large number of tumor cell types, including gliomas. VEGF is a major regulator of angiogenesis and has mitogenic activity that is specific for vascular endothelial cells. Based on this information, EPO and VEGF HREs, whose sequences are known (Semenza et al. 1998, Chest 114:40S–45S) were chosen for the design and testing of a hypoxia/HIF-responsive promoter.

The EPO HRE sequence, SEQ ID NO:1, GCCCTACGTG CTGTCTCACA CAGCCTGTCT GAC, and the VEGF sequence, SEQ ID NO:2, CCACAGTGCA TACGTGGGCT CCMCAGGTC CTCTT, along with additional sequences to facilitate their cloning into the pBI vector, were synthesized by standard oligonucleotide synthesis procedures. These HRE were then used to construct the vectors in Example 5.

Example 5

Generation of Hypoxia/HIF-Inducible Expression Vectors

The large size and limited unique cloning sites of currently available adenoviral vectors restrict their usefulness in the multiple subcloning steps required for the construction of the HYPR-Ad series of viruses. Therefore, the construction and testing of hypoxia/HIF-dependent promoters and the subsequent subcloning of the E1 and adjuvant therapeutic gene was performed using modified pBI and pBI-GL mammalian expression vectors (Clontech, Palo Alto, Calif., FIG. 2). The resulting gene cassette within the modified pBI plasmid is subsequently used in the construction of the recombinant HYPR-Ad series of adenoviruses.

The pBI vector can be used to express two genes of interest from a bidirectional tetracycline (tet) responsive promoter which contains 7 copies of the tet-responsive elements flanked by two minimal CMV. The pBI-GL vector, contains the luciferase and LacZ/β-Gal reporter genes under the regulation of the same promoter. The pBI and pBI-GL mammalian expression vectors were modified such that the tet-responsive elements were replaced with hypoxia/HIF-responsive elements (HRE). Xho1 recognition sites were introduced into the pBI and pBI-GL plasmids 5' and 3' of the tet-responsive element by site directed mutagenesis (QuikChange Site-Directed Mutagenesis Kit, Stratagene, La Jolla, Calif.). The tet-response element was then removed by digestion with Xho1. Oligonucleotides that span the HRE within the 5' flanking region of the VEGF gene and the 3' flanking region of the EPO gene were synthesized (see example 4), concatemerized and then cloned in tandem (head to tail orientation) into the Xho1 site of the modified pBI and pBI-GL TET vectors. Constructs designated pBI-HRE and pBI-GL-HRE which contain one to six tandem copies of the VEGF or EPO HREs in both the 5' and 3' orientations were generated.

Example 6

Testing of Bi-Directional Hypoxia/HIF-Inducible Reporter Gene Expression

The pBI-GL-HRE constructs were examined for their ability to bidirectionally express the luciferase and β-gal reporter genes in response to hypoxia and/or HIF. In addition, the influence of copy number and orientation on the basal activity and hypoxia specific induction of the reporter genes was also examined. Finally, the basal activity and induction capability of the VEGF versus EPO HRE's were compared in order to determine a response element that confers optimal regulation in glioma cell lines.

Initially, the reporter gene activities of the 24 pBIGL-HRE constructs under normoxic vs. hypoxic conditions were examined in the LN229 glioma cell line. The constructs were transiently transfected into the LN229 cells using GenePorter transfection reagent (Gene Therapy Systems, San Diego, Calif.). The cells were allowed to recover from the transfection procedure overnight and were then incubated under normoxic (20.8% $O_2$) or hypoxic (1% $O_2$) conditions for 48 h. The original pBI and pBI-GL plasmids were used as negative controls for these experiments. Luciferase and β-gal enzymatic activities were measured using a commercial assay (Tropix Dual-Light chemiluminescent reporter gene assay system, Applied Biosystems, Foster City, Calif.). Enzymatic activities were then normalized per microgram of total protein in the cellular extracts using a modified Bradford protein assay (Bio-Rad, Hercules, Calif.).

Based on the data obtained in LN229 cells, 8 of the 24 constructs (pBI-GL VEGF-5L, 6L, 3R, 4R, 5R, and 6R and pBI-GL EPO-3L and 6L) were selected for further analysis. These 8 constructs displayed the lowest levels of reporter gene activity under normoxic conditions and the highest bidirectional induction of reporter gene activity in response to hypoxia. To confirm and extend the bi-directional reporter gene activity data obtained in LN229 cells, these 8 constructs were also tested in two other glioma cell lines (U251MG, U138MG) under normoxia and hypoxia (1% $O_2$) (FIGS. 3A–3D).

These results demonstrate that the VEGF and EPO HRE can induce bi-directional gene expression under hypoxic conditions. Importantly, high induction was exhibited when the tandem copies were facing both in the 5' or 3' direction (L versus R in the construct name), suggesting that the bi-directional induction of the reporter genes was not dependent upon the orientation of the tandem copies. Finally, the background expression of these constructs under normoxic conditions was minimal and not significantly greater than that seen with the pBI-GL vector.

Example 7

Hypoxia-Inducible Alkaline Phosphate Expression

A plasmid construct containing an alkaline phosphatase gene under the control of a hypoxia/HIF-inducible promoter was transfected into LN229 glioma cells. Clones were placed into individual wells of a 48-well plate and exposed to either normoxic or hypoxic conditions. Clones that assayed positive for expression of alkaline phosphatase under hypoxic conditions and negative under normoxic conditions were retained and examined further. Clones that tested positive under both normoxic and hypoxic conditions were discarded.

Example 8

Hypoxia and/or HIF-Responsive Viruses

Two commonly used methods to generate recombinant adenoviruses involve either homologous recombination in mammalian cells or direct ligation of DNA fragments in the adenoviral genome. Recently, a new system, referred to as pAdEasy (Stratagene, La Jolla, Calif.), (He, T. C. et al., [1998] Proc. Natl. Acad. Sci. 95:2509–14) has allowed for the recombination procedures to be performed in bacteria. In the pAdEasy system a gene of interest is first cloned into a shuttle plasmid whose polylinker is flanked by adenoviral sequences. These flanking adenoviral sequences allow homologous recombination with an adenoviral plasmid which contains all of the adenoviral genome except for the E1 and E3 viral regions. The recombination product is then transfected into the 293 packaging cell line (ATCC, Rockville, Md.) to generate recombinant adenovirus. In order to establish the pAdEasy system within the context of this invention, a replication-deficient adenovirus which expresses the green fluorescent protein (GFP) was generated and GFP expression was verified in infected LN229 brain tumor cells.

Example 9

Generation of Replication-Competent Recombinant Adenovirus HYPR-Ad with the pAdEasy System The following describes the generation of conditional attenuated adenoviruses that selectively replicate under conditions of hypoxia and/or HIF activation by construction of a recombinant adenovirus with the adenoviral E1A gene under an exogenous hypoxia/HIF-dependent promoter (HRE coupled to minimal CMV promoters).

Adenoviruses are DNA viruses that infect both dividing and quiescent cells. Re-entry of infected quiescent cells into the cell cycle is required for viral DNA replication and ultimately, viral progeny production. The expression of E1A gene products is essential for these viral functions and adenoviruses which lack the E1A gene region are replication-deficient. The adenoviral E1A gene is the first transcription unit to be expressed from a constitutively active promoter region. Products of the E1A gene exhibit a wide range of biological activities including the modulation of cellular and viral transcription (including the induction of E1B gene transcription) and the induction of DNA synthesis in quiescent cells. However, deregulation of cell growth control by E1A induces apoptosis through p53 dependent and independent mechanisms and ultimately interferes with viral progeny production. The prevention of apoptosis during wild type adenovirus infection is mediated by expression of the adenoviral E1B gene products. The E1B gene encodes two proteins, 21K and 55K, which function independently to inhibit E1A-induced apoptosis. The E1B 21K protein is homologous in sequence and function to the Bcl-2 family of apoptosis regulators and blocks E1A induced apoptosis as well as many other apoptotic stimuli. The infection of cells with adenoviruses lacking E1B 21K function leads to the appearance of extensive nuclear and viral DNA degradation (deg phenotype) and enhanced cytopathic effect (cyt phenotype). The E1B 55K, in conjunction with the adenoviral E4-orf6 gene product, has two functions during viral production: to directly interact with and inactivate p53, and later in viral production to facilitate the transport of viral late mRNA while inhibiting the transport of most cellular mRNA.

Figure 7:
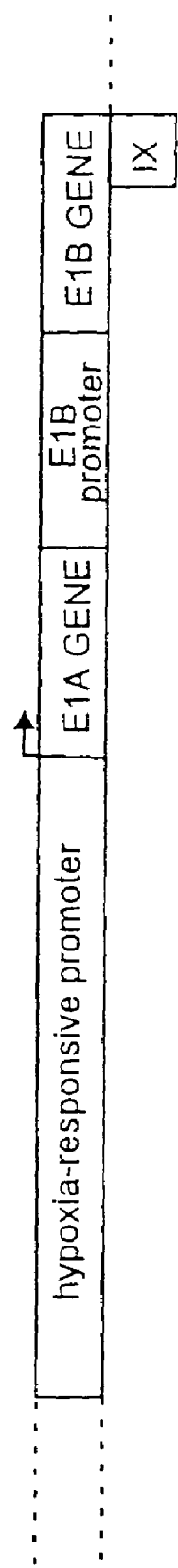
FIG. 7 shows a schematic representation of the subcloning of the E1 gene cassette into the pAdEasy adenoviral vector. See examples 8–9 for further description and experimental details.

Adenoviruses which lack E1B 55K function, such as ONYX-015, are capable of efficient viral progeny production in many human cells independent of the functional status of p53. However, these mutant viruses exhibit drastically reduced viral yield in a subset of human cell lines. It is currently believed that this mutant phenotype results primarily from the absence of the late mRNA transport function of E1B 55K and that some cell lines may have compensatory pathways that the mutant virus can utilize. Based on the important role of the E1B gene products during viral progeny production, HYPR-Ad's as well as an Ad-CMV-E1 can be generated that contain this gene. This can be accomplished by introducing into an E1 deleted adenoviral vector, a DNA cassette containing the adenoviral E1 genomic region (E1A, E1B, and IX genes) in which the E1A gene is regulated by an exogenous hypoxia-inducible promoter (FIG. 7).

Figure 6:
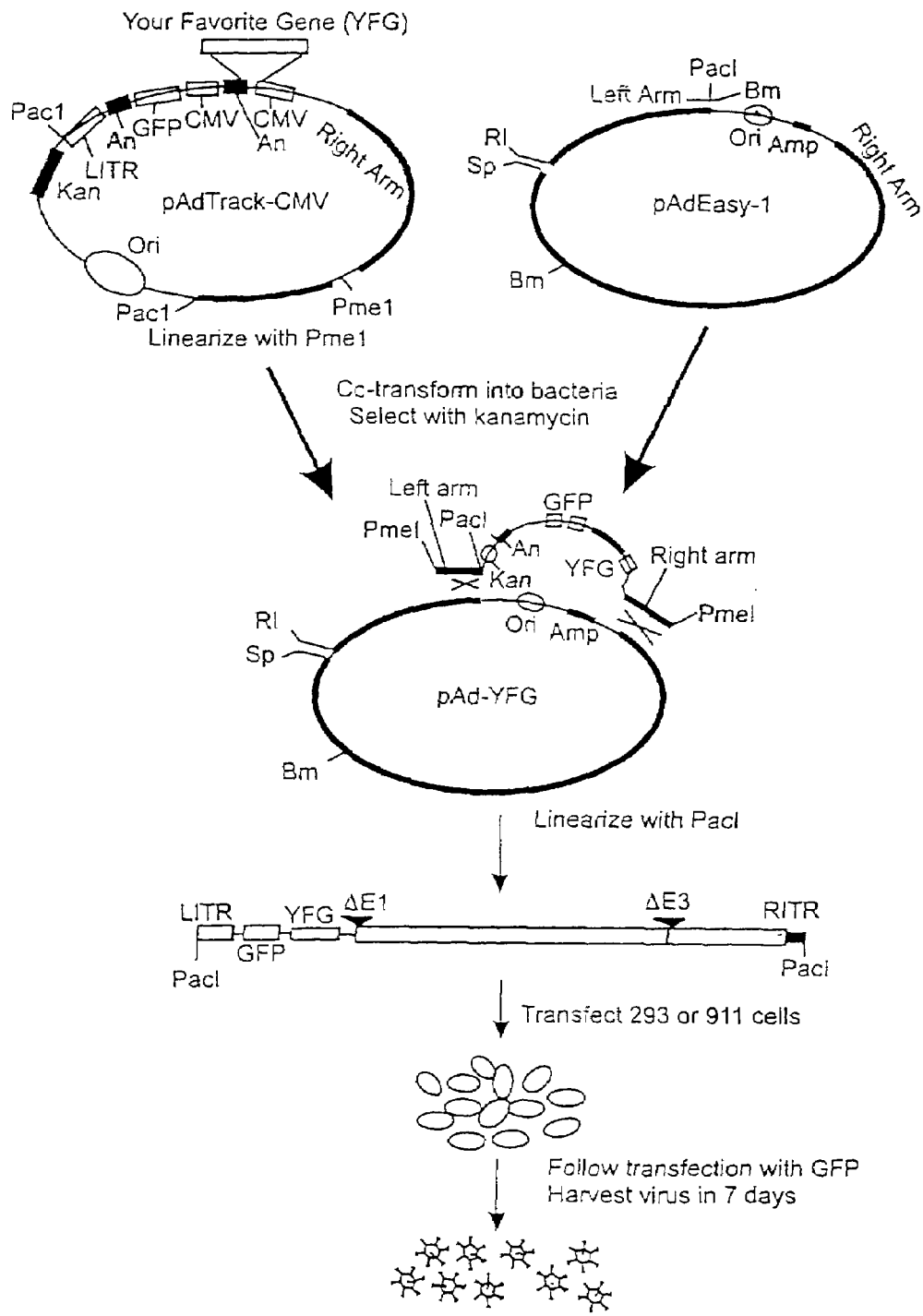
FIG. 6 shows a schematic outline for construction of recombinant viruses. See examples 8–9 for further description and experimental details.

The genomic E1 region from nucleotides 501 to 4105 of adenovirus type 5 (encompassing the E1A gene region and the E1B and IX transcription units) were amplified by Pfu Turbo DNA polymerase (Stratagene, La Jolla, Calif.) using DNA extracted from the dl309 virus (which is wild type for the E1 gene region but has a substitution in the E3 gene region making it safer for laboratory use, from Dr. E. Harlow, Massachusetts General Hospital, Boston, Mass.). The resulting 3.6 Kb amplified DNA product was cloned downstream of a hypoxia/HIF-inducible promoter containing 6 VEGF HRE coupled to a minimal CMV promoter (derived from pBI-VEGF-6R). The HRE-CMV-E1 cassette was subsequently subcloned in the adenoviral shuttle vector (pShuttle) (FIG. 6). Recombinants were selected for kanamycin resistance and recombination was confirmed by multiple restriction endonuclease analyses. In the final phase, the recombinant adenoviral plasmids were linearized with Pac1 to expose the inverted terminal repeats and then transfected using lipofectamine reagent (Gibco-BRL, Gaithersburg, Md.) into the 293 packaging cell line. The resulting virus (HYPR-Ad#1) was harvested using standard protocols and characterized as described below. For comparative purposes an adenovirus in which the E1 region is regulated by a constitutively active CMV promoter (Ad-CMV-E1) was also generated.

Example 10

Figure 8A:
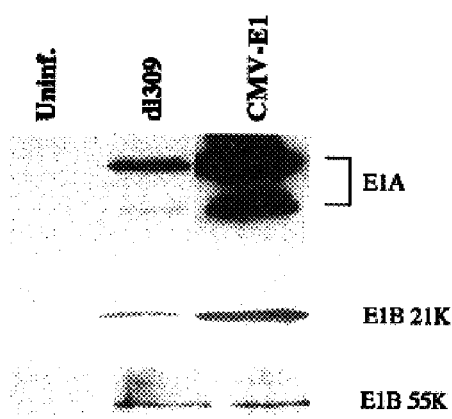
FIGS. 8A–B show expression of recombinant viral gene products in transfected tumor cell line (glioma LN229) by western blot analysis.
Figure 8B:
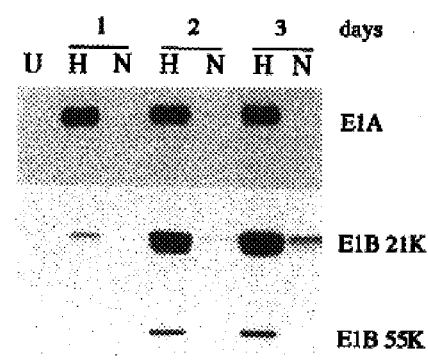

Expression of Recombinant Viral Gene Products in Transfected Cells Under Hypoxic and Normoxic Conditions The E1A and E1B viral proteins are constitutively expressed in the human 293 cells as a result of the stable integration of these genes in the 293 cellular genome. Therefore, 293 cells cannot be used to confirm expression of these viral proteins. To confirm expression of these proteins from the recombinant adenoviruses, U251MG and LN229 cells were infected with the Ad-CMV-E1 and HYPR-Ad#1. Protein expression was examined by Western blotting of infected cells using monoclonal anti-Adenovirus Type 5 E1A, E1B 55 Kd and 21 Kd antibodies. Uninfected cells served as negative control (FIGS. 8A–B). E1A is activated by hypoxia in HYPR-Ad#1. E1A is known to activate the expression of other viral promoters including early E1B gene regulation. This explains the increased expression of E1B gene products under hypoxia. Late E1B gene regulation involves other factors and may explain the increased expression of E1B 21K under normoxia at 2–3 days post-infection.

These experiments demonstrate that the recombinant adenoviruses were able to express constitutively (Ad-CMV-E1) or conditionally (HYPR-Ad#1) E1A and E1B gene products. This demonstrates that the hypoxia-dependent regulation seen in the transient reporter gene assays is maintained in the context of the adenovirus genome.

Example 11

Cytolysis of Tumor Cells in a Hypoxia Dependent Manner

Figure 9A:
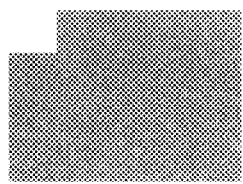
FIGS. 9A–D show the cytolysis of tumor cells in an hypoxia dependent manner.
Figure 9B:
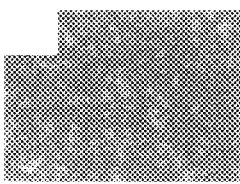
Figure 9C:
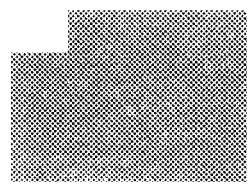
Figure 9D:

The ability of HYPR-Ad#1 and Ad-CMV-E1 to induce cytolysis in the LN229 glioma cell line was determined by infection with increasing volumes of the two viruses (FIGS. 9A–D). One set of cells was incubated under normoxic conditions (20.8% $O_2$) and the other set of cells was incubated under hypoxic conditions (1% $O_2$). As a negative control, uninfected LN229 gliomas cells were used. The cells were examined daily for evidence of cytopathic effect (CPE). The use of sub-saturating viral concentrations for infection enabled us to follow the progression of CPE over time. These preliminary data indicated that after 6 days of normoxia or hypoxia (FIG. 9A) mock infected LN229 cells are confluent. A small number of cells rounded-up and appeared as dark spots surrounded by a white halo. Some of these cells were dividing and some detached from the monolayer, a typical behavior of this cell line at confluency. Cells infected with Ad-CMV-E1 (FIG. 9B) showed clear signs of CPE, many cells rounded-up and detached from the monolayer. The morphology of cells infected with HYPR-Ad#1 and maintained under normoxia was similar to that of uninfected cells, with perhaps a slight increase in round-up cells (FIG. 9C). In contrast, most cells infected with HYPR-Ad#1 and maintained under hypoxia (FIG. 9D) underwent cytolysis similar to Ad-CMV-E1 infected cells. These results indicate that HYPR-Ad#1 is conditionally replication-competent since it induced CPE under hypoxic conditions.

Example 12

Delivery of Recombinant Virus to Brain Tumors

Figure 10:
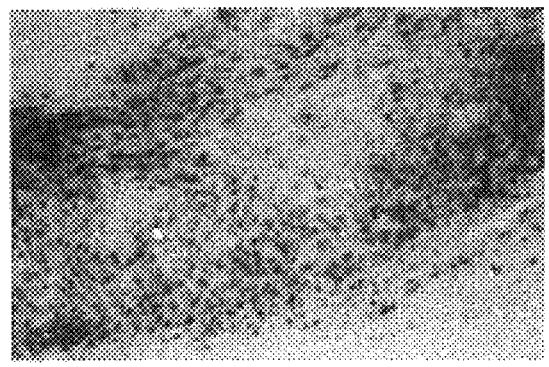
FIG. 10 shows the delivery of recombinant virus to brain tumors. Section of glioma from transplanted rat glioma tumor cells infected LacZ expressing replication-deficient adenovirus stained for β-gal expression. See example 12 for further description and experimental details.
Figure 11A:
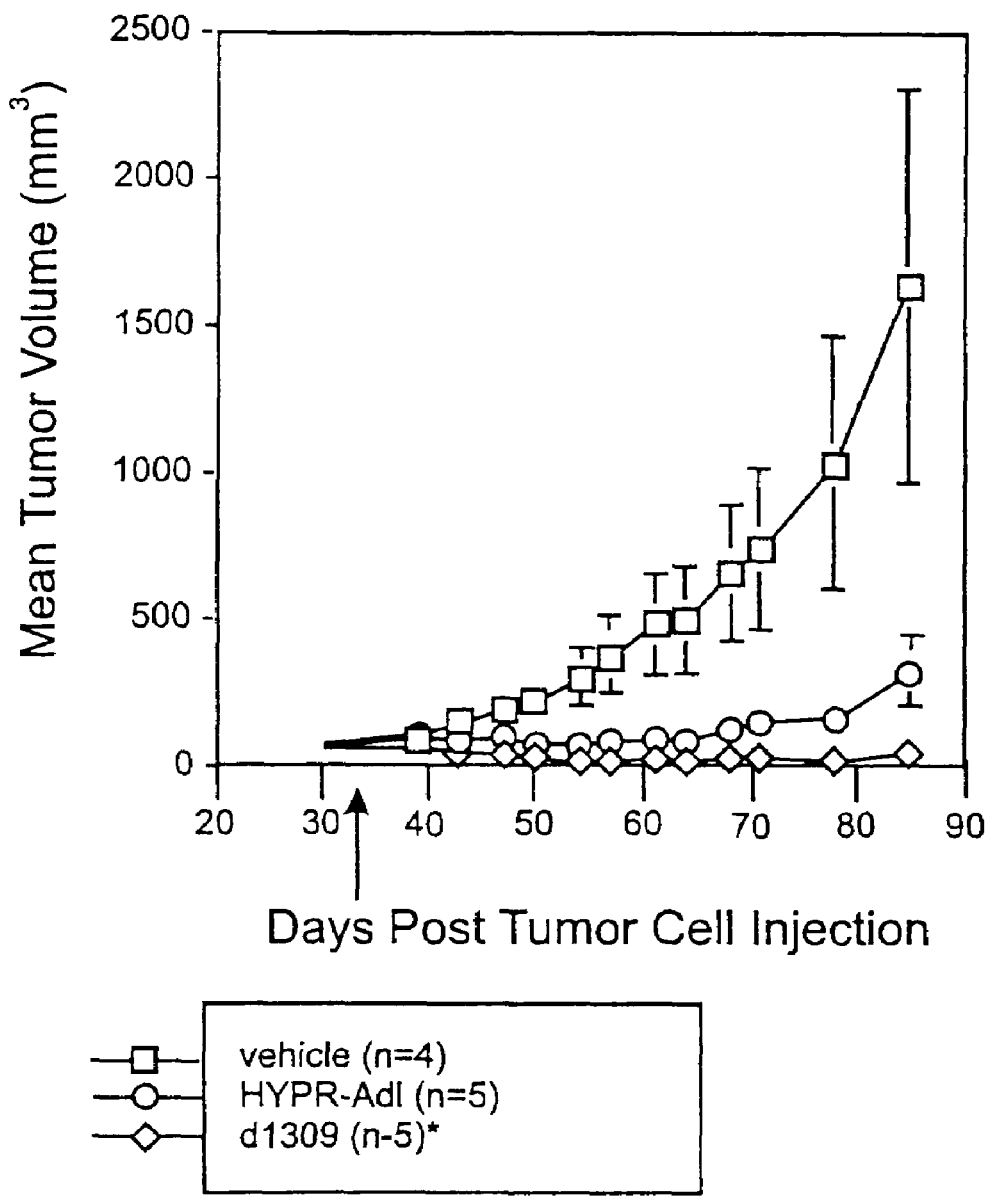
FIGS. 11A–11B show the results of animal studies.
Figure 11B:
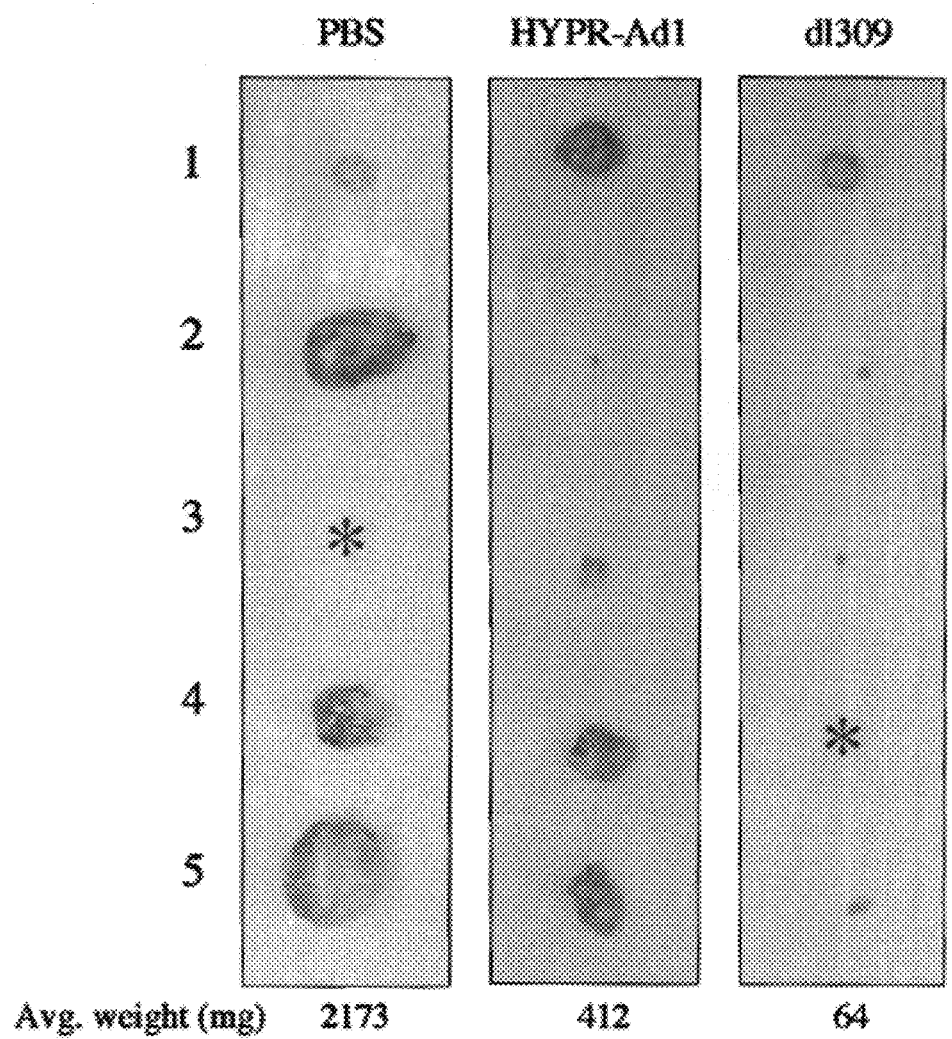

The experiments described in this section involve intracerebral injection of tumor cells and adenovirus into nude mice by stereotactic technique. Rat glioma tumor cells ($5 \times 10^4$ cells, 5 µl volume) were stereotactically implanted in the brain of syngeneic Fisher 344 rats. Eleven days later, a replication-deficient adenovirus expressing LacZ ($1.8 \times 10^{10}$ particles, 24 µl volume) was co-injected with inert colloidal carbon particles (0.5 µl) into the tumor using the same stereotactical co-ordinates as for tumor cell injection. The rat was sacrificed 24 h after virus injection and the brain extracted and analyzed by serial sectioning. The section was processed to detect β-gal expression and cells expressing the virally encoded enzyme were visible in the blue area. Black grains are colloidal carbon particles deposited along the needle track. This section revealed that 60–80% of the tumor cells along the needle tract were infected and expressed the LacZ protein. See FIG. 10 for results.

Example 13

Identification of Compounds that Modulate the Hypoxia-Inducible Pathway

Equal numbers of cells derived from a clone of LN229 glioma cells transformed with an expressible plasmid construct containing a hypoxia/HIF-responsive promoter operably linked to the gene for alkaline phosphatase are added to the wells of a 96-well microtiter plate. Cells are incubated overnight at 37° C. to allow them to adhere. The microtiter plates and cells containing the reporter construct are simultaneously equilibrated to a desired $O_2$ concentration, i.e., hypoxic or normoxic, or treated with a compound known to induce transcription of genes driven by the hypoxia/HIF-responsive promoter.

An appropriate amount of test compound diluted into assay buffer is then placed into each well. During initial screens each well has a different test compound except for the control wells which have either no compound or an inactive compound. After a selected period of time the reactions are assayed for alkaline phosphatase activity. The alkaline phosphatase activity can be detected visually or spectrophotometrically. Compounds which reduce or increase the level of expression of alkaline phosphatase under conditions which induce hypoxia-responsive genes are classified as modulators of the hypoxia/HIF-inducible pathway.

Compounds that test positive in the initial screening assay are further examined by performing the same assay as described above, except for varying the concentration of the test compound to determine the concentration of compound that inhibits 50% of the level of expression of the alkaline phosphatase activity ($IC_{50}$). Compounds that have an $IC_{50}$ in these assays of less than 500 µm are preferred; compounds that have an $IC_{50}$ of less than 100 µm are more preferred; and those that have an $IC_{50}$ of less than 10 µm are highly preferred.

Example 14

In vivo Evaluation of Compounds Modulating Expression of Hypoxia-Responsive Genes Experimental tumors are grown in immunocompromised mice by placing cells derived from a clone of LN229 glioma cells transformed with an expressible plasmid construct comprising a hypoxia/HIF-responsive promoter operably linked to the gene for alkaline phosphatase. When tumors have reached a particular size, a compound which has been shown to modulate induction of hypoxia-responsive genes in vitro is administered to the mice. An inactive compound, or no compound, is administered to other mice in the experimental group as a negative control.

After a determined time, the experimental tumors are removed from the mice, and sections of these tumors are assayed for expression of alkaline phosphatase. Control tumors will show pockets of alkaline phosphatase expression, but the majority of the cells in the tumor will not show alkaline phosphatase expression. Expression of alkaline phosphatase in an experimental tumor treated with a compound by higher percentage of cells than is seen in the control tumor confirms that the compound is capable of reaching tumor cells and is active in vivo to stimulate hypoxia-responsive gene transcription. However, alkaline phosphatase expression by a lower percentage of cells than is seen in the control tumor confirms that the compound is capable of reaching tumor cells and is active in vivo to inhibit hypoxia-responsive gene transcription.

Example 15

Reduction of the Growth of Xenografted Glioma Cells in Immunocompromised Mice

LN229 cells were implanted subcutaneously into the left flank of nu/nu mice. When the average tumor volume [volume=(length×width$^2$)/2] reached 75 mm$^3$ (arrow), the mice were divided into three groups and $0.66 \times 10^8$ pfu of adenovirus (HYPR-Ad#1 or d1309) or PBS (vehicle) was injected daily for five days. Forty-nine days following the injection protocol the mice were sacrificed (due to the large size of the PBS injected tumors) and the tumors were harvested. One of the vehicle mice died immediately following the completion of the injection protocol due to an unknown cause and one of the d1309 mice was sacrificed on day 57 due to excessive weight loss related to an eye infection. We found no difference in the growth of LN229 tumors that were injected with PBS versus not injected.

At the time of harvest the average size of the HYPR-Ad#1 injected tumors (circles) were 5.3 times smaller than PBS (squares) injected tumors. The d1309 injected tumors (diamonds) were 34 times smaller than PBS injected tumors. The d1309 injected tumors were 6.4 times smaller than HYPR-Ad#1 injected tumors.

Example 16

Construction of Second-Generation HYPR-Ad Recombinant Viruses

In order to augment the antitumor activities of HYPR-Ad, a series of the second-generation recombinant viruses that encode genes which regulate or modulate replication of the virus and/or encode a therapeutic protein with anti-tumor activity were designed and developed. The resulting second-generation viruses were designed to exhibit enhanced cell killing effects due to the combined action of viral-mediated killing of hypoxic/HIF-active tumor cells and the specific activity of the expressed adjuvant therapeutic molecule. For example, HYPR-ADP-Ad contains the Adenovirus Death protein (ADP) gene which can specifically be expressed in the tumor microenvironment. This protein was chosen because ADP is known to promote the cytolysis of infected cells, release of viral progeny from the infected cells, and the spread of progeny virus to surrounding cells. It is expected that the HYPR-Ad viruses containing the gene encoding ADP will result in an increase in the anti-tumor efficacy of the virus. To generate HYPR-ADP-Ad, the Ad type 5 E1 gene region was amplified by PCR using d1309 wild type Ad template DNA and then cloned downstream of a novel bi-directional hypoxia/HIF responsive promoter composed of six tandem copies of the HRE from the VEGF gene. The result is the adenoviral E1A replication gene under the direct regulation of the bi-directional hypoxia/HIF responsive V6R promoter while the E1B region was restored with its endogenous regulatory elements. The ADP gene was then amplified by PCR using d1309 template DNA and cloned into the left arm of the promoter, thereby creating HYPR-ADP-Ad. The design of the virus is shown schematically in FIG. 13.

Figure 14A:
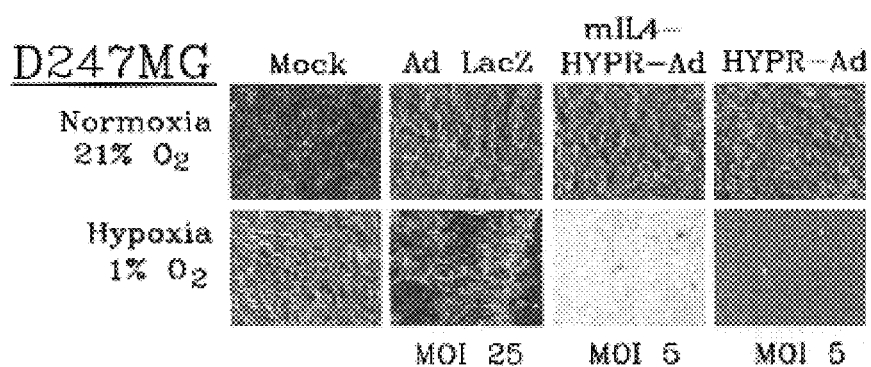
FIGS. 14A and 14B show that HYPR-IL-4-Ad conditionally lyses tumor cells under hypoxic but not normoxic conditions. D247 and U251MG glioma cells were monitored for cell lysis and detachment (CPE) under normoxia (21% $O_2$) versus hypoxia (1% $O_2$) after infection with the replication-defective AdLacZ, HYPR-IL-4-Ad, or mock infected. Note, as expected, HYPR-IL-4-Ad conditionally kills cells under hypoxia at an MOI similar to the parental virus, HYPR-Ad.
Figure 14B:
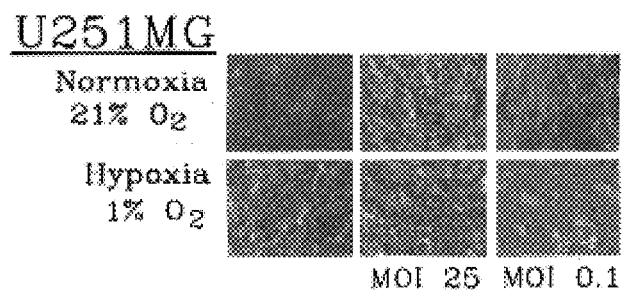
Figure 15A:
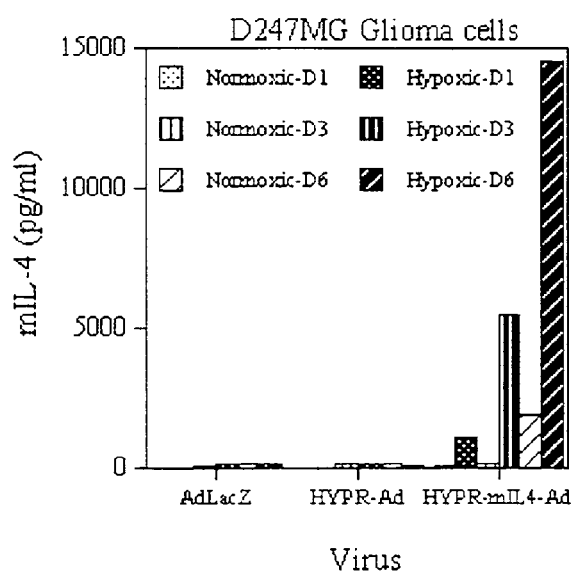
FIGS. 15A and 15B illustrate the conditional expression of IL-4 by HYPR-IL-4-Ad in two infected glioma cells maintained under hypoxia. D247MG and LN229 glioma cells were infected with the replication-defective AdLacZ, the parental HYPR-Ad or HYPR-IL-4-Ad at MOI 1.0 and then maintained under normoxic (21% $O_2$) or hypoxic (1% $O_2$) conditions for 6 days. On days 1, 3, and 6 post-infection the media supernatant was collected and the amount of IL-4 was quantified (pg/ml) using a commercially available ELISA (Pierce, Rockville, Ill.). Note, as expected, only the media supernatant collected from HYPR-IL-4-Ad infected cells maintained under hypoxia contains IL-4.
Figure 15B:
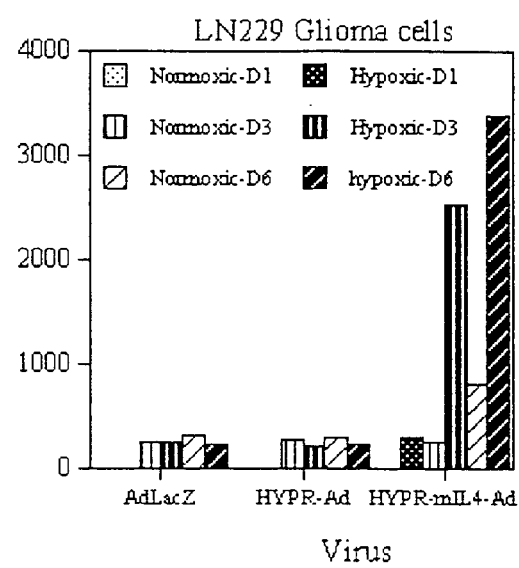

Another example of the second-generation recombinant virus of the invention is HYPR-IL-4-Ad which contains the anti-tumorigenic interleukin-4 (IL-4) gene. IL-4 is known to exhibit multimodal anti-tumor activity including the induction of a host immune response against the tumor and inhibition of tumor angiogenesis against a wide range of tumor types. This recombinant virus represents the first example of a trimodal viral gene therapy strategy consisting of virus mediated cytolysis, immunogene, and anti-angiogenic therapy. Furthermore, the local expression of IL-4 in the tumor microenvironment via HYPR-Ad is important as systemic IL-4 expression has serious side effects and the IL-4 protein has a short half life. To generate HYPR-IL-4-Ad, the IL-4 gene was cloned into the left of the promoter shown in FIG. 13 using standard protocols known in the art. The results shown in FIGS. 14A and 14B demonstrate that the recombinant virus, HYPR-IL-4-Ad, indeed express IL-4 in a hypoxia dependent manner. Further, HYPR-IL-4-Ad is capable of killing tumor cells under hypoxic but not under normoxic conditions as shown in FIG. 15.

Additional example of the second-generation recombinant virus is HYPR-miniTSP-1-Ad which contains a gene encoding a mini-thrombospodin-1 (miniTSP1). TSP-1 is a known anti-angiogenic protein which exhibits potent anti-tumor activity against a wide range of tumor types. TSP-1 is a 450 kDa homotrimeric matrix glycoprotein that functions as an endogenous angiogenesis inhibitor and suppresses both tumor growth and metastasis in vivo. The interaction of TSP-1 with the cellular CD36 receptor on microvascular endothelial cells induces endothelial cell apoptosis as well as the inhibition of endothelial cell proliferation, migration, and organization into blood vessels. Targeting tumor angiogenesis using this recombinant virus is particularly attractive since the expression of miniTSP-1 is expected to inhibit the formation and growth of the tumor microvasculature leading to new areas of hypoxia within the tumor. This can result in further propagation and spread of the HYPR-miniTSP-1-Ad virus through the tumor mass. Therefore, the therapy employing this recombinant virus will target three distinct cell populations within the tumor microenvironment: hypoxic tumor cells, normoxic tumor cells, and the tumor microvasculature. The local expression of TSP-1 in the tumor microenvironment via HYPR-miniTSP-1-Ad is important as the homotrimeric structure and the large size of TSP-1 severely limit its delivery to tumors by systemic administration. Thus, HYPR-miniTSP-1-Ad can be used as a therapy for a broad range of tumors which develop hypoxia or have active HIF regardless of their tissue origin or genetic composition. To generate HYPR-miniTSP-1-Ad, a mini-thrombospondin-1 (mini-TSP-1) gene construct containing the secretion signal of TSP-1 fused in frame with the three TSP-1 repeats, was cloned into the left arm of the promoter shown in FIG. 13.

Example 17

Non-Invasive Detection of Cell Hypoxia in Intact Live Animals

The present invention also provides novel means to detect cell hypoxia in intact live animals in a non-invasive manner. Hypoxia is not only associated with a number of pathological conditions such as cancer and ischemia but also with specific developmental steps during embryogenesis. The ability to monitor these events in a non-invasive fashion would aid in understanding the role of hypoxia during normal organogenesis as well as serve as an early indicator of pathogenesis. For example, hypoxia can be used as a measure in an animal containing a reporter gene under the control of a hypoxia/HIF-responsive element(s) to detect non-invasively early cancer development in animals. These animals can be generated by various means (xenograph, carcinogenesis or transgenic animal models) as well as being used subsequently to monitor the efficacy of anti-cancer drugs.

Figure 4A:
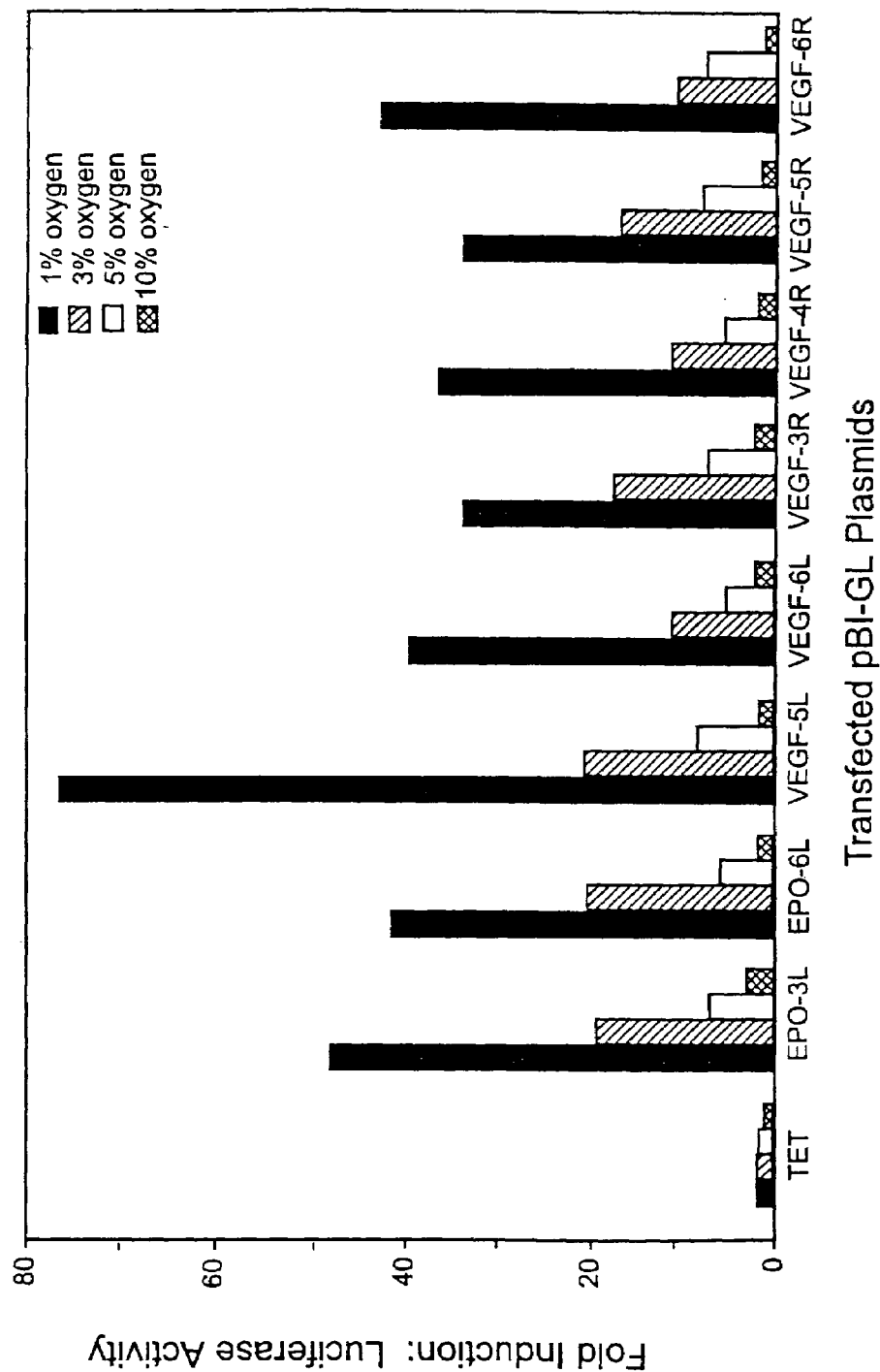
FIGS. 4A–B show the hypoxia induced expression of constructs in transfected tumor cell lines under variable oxygen partial pressure. VEGF or EPO-3,4,5,6 refers to the number of tandem repeats in the constructs, L for 5' orientation, and R for 3' orientation.
Figure 4B:
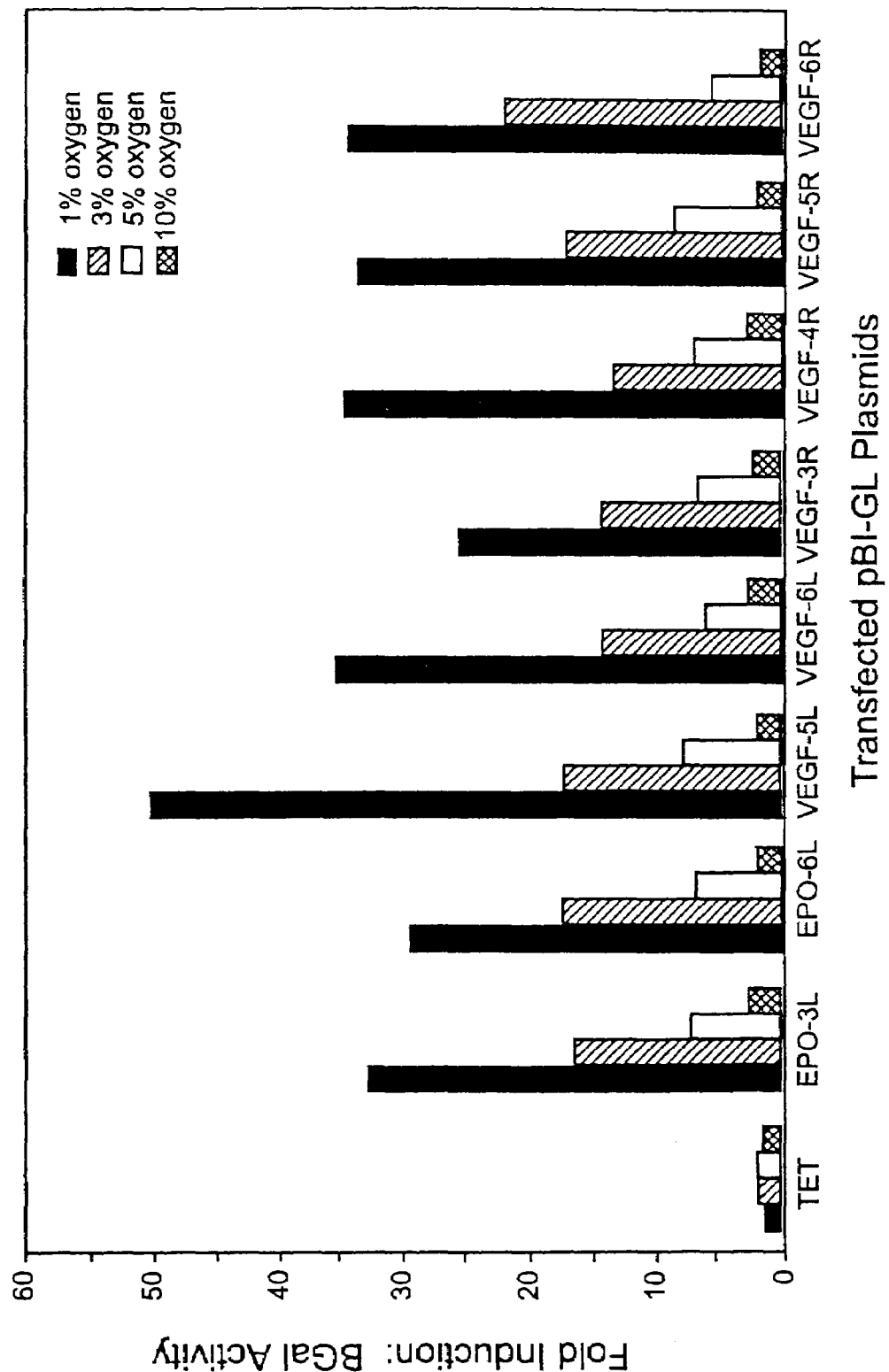
Figure 5A:
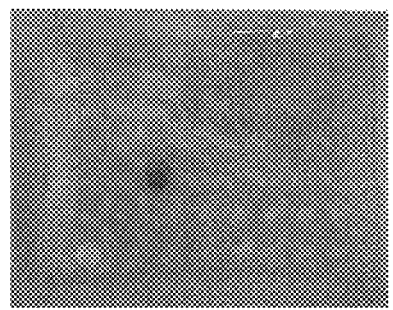
FIGS. 5A–B show the results from assays for alkaline phosphatase enzyme activity on clones derived from a human glioma cell line stably transfected with a construct having a hypoxia/HIF-responsive element operably linked to a promoter which is operably linked to the reporter gene alkaline phosphatase.
Figure 5B:
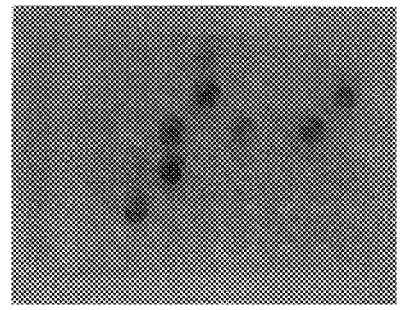

This aspect of the invention is based on the detection by imaging the activity of hypoxia-inducible transcription factor (HIF) in cells in intact animals. This can be achieved by stable genetic engineering of cells so that they express a reporter gene that is activated by HIF (referred hereinafter as "HIF reporter cells"). The HIF-activated reporter gene encodes a product that can be detected by imaging (referred hereinafter as "HIF-imaging reporter"). Examples of the reporter genes are luciferase gene or genes encoding fluorescent proteins (GFP, RFP, etc). Luminescence or fluorescence can be detected non-invasively by a CCD camera system on a live anesthetized animal. The procedure can be repeated over time during the life span of the animal. The specific constructs that can be used for the procedure are the reporter constructs described in Post and Van Meir (2001) Gene Therapy 8: 1801–1807. They consist of hypoxia/HIF-responsive elements placed in between two minimal CMV promoters oriented in opposite directions. Each promoter directs expression of a different reporter gene. For example, one is the luciferase gene and the other is the LacZ gene (see FIGS. 2–4).

Figure 16A:
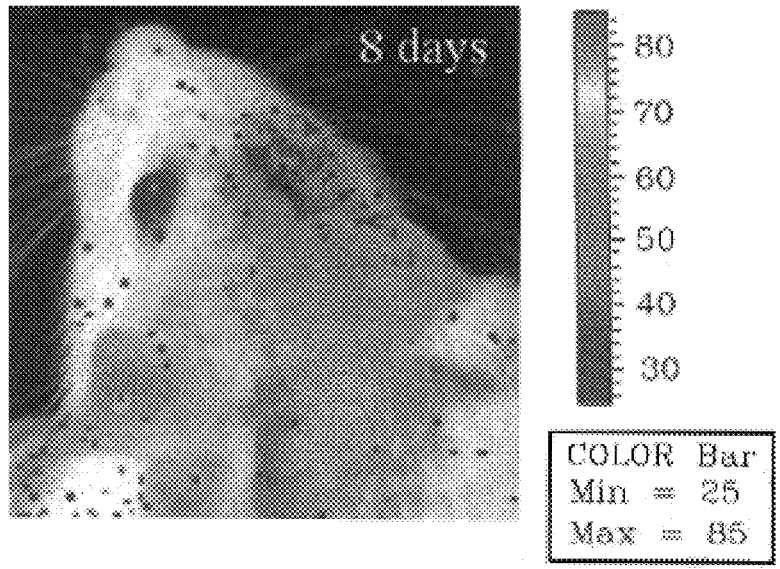
FIGS. 16A–B show examples of imaging of brain tumor development in rats containing the HIF-imaging reporter of the invention, which demonstrate that these animals can provide information regarding early tumor growth, size, and location. Two rats received intracranial implantation of 10,000 9L glioma cells stably transfected with V6L in the right hemisphere. V6L is a bi-directional HIF-responsive reporter construct containing the LacZ and luciferase gene (Post and Van Meir 2001 Gene Therapy 8:1801–1807). Luciferase activity was monitored in animals 8 and 11 days post tumor cell implantation after luciferin injection with a Xenogen COD camera system. Intensity of light emitted (a measure of HIF expression) was monitored by the color scheme on right. In this glioma model tumor growth is usually assessed by neurological symptoms at days 15–21 and animals die within a few days thereafter.
Figure 16B:
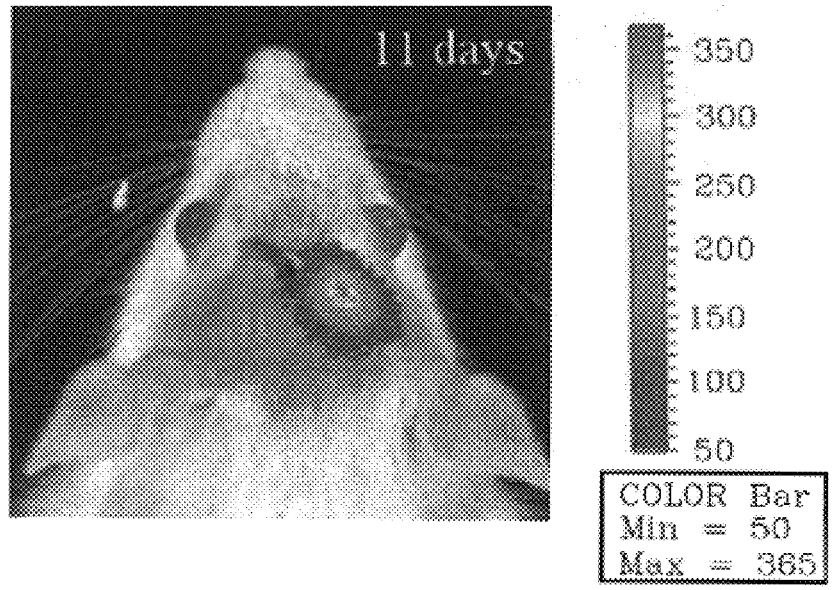

Two different approaches can be utilized to generate animals harboring the reporter gene constructs described above. First, genetically engineered cells that contain the HIF imaging reporter gene construct are implanted in animals and their expression monitored. An example is the implantation of tumor cells in the animal brain and monitoring of tumor growth by imaging hypoxia/HIF-driven luciferase expression as shown in FIGS. 16A and 16B. Second, transgenic animals harboring the HIF imaging reporter gene construct can be generated and monitored by imaging for the HIF imaging reporter expression. These animals are useful for studying embryogenesis and pathological conditions such as ischemia, wound healing, tumor growth etc. For example, a tumor can be induced in these transgenic animals by a protocol known in the art (e.g., carcinogen) and the tumor development and localization can be detected by imaging. Any changes in tumor growth in response to genetic background (genetic susceptibility), environmental exposure (carcinogenesis or chemoprevention) or anti-cancer treatments (drug development) can be monitored over time. These animals can be used as rapid model systems for evaluating any intervention strategies in preclinical trials. The use of a live intact animals in a non-invasive manner for the purposes described herein represents a major improvement over the currently available methods which require killing the animals and then staining for HIF expression or indirect measures of hypoxia by pimonidazoles or invasive implantation of oxygen measuring electrodes. Current methods relying on cell metabolism for imaging may indirectly be a measure of hypoxia but these rely on injection of radioactive compounds for PET imaging. The methods disclosed herein is specific to HIF and use imaging techniques that require no injections of compounds in animals (fluorescence) or injection of easily available and non-hazardous substrates (luciferin for luminescence). Further, the methods of the invention can be used to detect cancer development independent of the type of cancer or the specific genetic alterations that lead to a particular type of cancer. In contrast, most cancer detection and imaging techniques available to date are limited to the usage in specific types of cancer.

All references cited in the present application are incorporated in their entirety herein by reference to the extent not inconsistent herewith.

We claim:

1. A recombinant virus comprising one or more hypoxia and/or HIF responsive elements, wherein the hypoxia responsive element is capable of inducing bi-directional expression and wherein said one or more hypoxia and/or HIF-responsive elements are linked to a minimal promoter at each end, which element positively controls expression of a protein or peptide which is essential for replication of the virus such that said virus replicates in a hypoxia dependent manner, with the result that replication of said virus leads to cytolysis of hypoxic tissues and cells or cytolysis of cells and tissues containing an active HIF pathway.

2. The recombinant virus of claim 1 wherein the virus is an adenovirus, herpes virus, retrovirus, and picornavirus.

3. The recombinant virus of claim 2 further comprising a nucleic acid encoding a peptide having anti-angiogenic activity, whose expression is controlled by a hypoxia or HIF responsive element.

4. The recombinant virus of claim 3 wherein said cells or tissues are tumor cells or tumor tissues.

5. The recombinant virus of claim 4 wherein the virus is adenovirus type 5.

6. The recombinant virus of claim 5, wherein the peptide essential for replication of the virus is the EIA gene product.

7. The recombinant virus of claim 3 wherein the peptide having anti-angiogenic activity is selected from the group consisting of angiostatin, thrombospondin-1, thrombospondin-2, endostatin, platelet factor 4 (PF4), brain angiogenesis inhibitor 1 (BAI1), interleukin-4 (IL-4), ADAMTS, pigment epithelium-derived factor (PEDF) or fragments thereof.

8. The recombinant virus of claim 7, wherein the peptide having anti-angiogenic activity is interleukin-4.

9. The recombinant virus of claim 6 wherein the peptide is adenovirus death protein (ADP).

10. The recombinant virus of claim 7 wherein the anti-angiogenic peptide is a mini Thrombospondin-1 (miniTSP-1).

11. The recombinant virus of claim 1, wherein said minimal promoter is a cytomegalovirus minimal promoter.

12. A method of decreasing or removing an undesired tissue or cell comprising the step of infecting the hypoxic cell or tissue with the recombinant virus of claim 2, whereby the undesired cell or tissue is lysed.

* * * * *

SEQUENCE LISTING

```
<160> NUMBER OF SEQ ID NOS: 2

<210> SEQ ID NO 1
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 1
gccctacgtg ctgtctcaca cagcctgtct gac                                 33

<210> SEQ ID NO 2
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 2
ccacagtgca tacgtgggct ccaacaggtc ctctt                               35
```